(12) United States Patent
Kim et al.

(10) Patent No.: US 12,110,325 B2
(45) Date of Patent: Oct. 8, 2024

(54) TM4SF5-TARGETING HUMANIZED ANTIBODY AND USE THEREOF

(71) Applicants: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

(72) Inventors: Se Mi Kim, Daejeon (KR); Jung Weon Lee, Hanam-si (KR); Dongjoon Ko, Daejeon (KR); Junghwa Yoon, Daejeon (KR); Eunmi Kim, Seoul (KR); Seo Hee Nam, Daejeon (KR); Eun Ae Shin, Suwon-si (KR)

(73) Assignees: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 18/154,597

(22) Filed: Jan. 13, 2023

(65) Prior Publication Data
US 2023/0279104 A1  Sep. 7, 2023

(30) Foreign Application Priority Data
Jan. 14, 2022 (KR) .......................... 10-2022-0005907

(51) Int. Cl.
*C07K 16/28* (2006.01)
*A61P 43/00* (2006.01)
*C12N 15/63* (2006.01)

(52) U.S. Cl.
CPC .............. *C07K 16/28* (2013.01); *A61P 43/00* (2018.01); *C12N 15/63* (2013.01); *C07K 2317/565* (2013.01)

(58) Field of Classification Search
CPC .............. C07K 16/28; C07K 2317/565; C07K 2317/24; C07K 2317/33; C07K 2317/622; C07K 2317/73; C07K 2317/76; C07K 2317/77; A61P 43/00; A61P 1/16; A61P 35/00; C12N 15/63; A61K 39/3955; A61K 2039/505; A61K 2039/545; G01N 33/574; G01N 33/6893
See application file for complete search history.

(56) References Cited

U.S. PATENT DOCUMENTS 9,815,900 B2 * 11/2017 Kim .................. C07K 16/2863
2016/0002322 A1 * 1/2016 Kwon .................. C07K 16/28
530/387.3

FOREIGN PATENT DOCUMENTS

KR     10-0934706 B1   12/2009

OTHER PUBLICATIONS

Safeld. Isotype selection in antibody engineering. 2007. 25(12): 1369-1372. (Year: 2007).*
Hyeonjung Kim, et al., "TM4SF5 accelerates G1/S phase progression via cytosolic p27Kip1 expression and RhoA activity", Elsevier, Biochimica et Biophysica Acta, 2010, pp. 975-982, 1803.
Minkyung Kang, et al., "Cross-talk between TGFB1 and EGFR signalling pathways induces TM4SF5 expression and epithelial-mesenchymal transition", BJ www.biochemj.or, Biochem. J., 2012, pp. 691-700, 443.
Sin-Ae Lee, et al., "Tetraspanin TM4SF5 mediates loss of contact inhibition through epithelial-mesenchymal transition in human hepatocarcinoma", JCI, The Journal of Clinical Investigation, Apr. 2008, pp. 1354-1366, vol. 118, https://doi.org/10.1172/JCI33768.
Elvin A. Kabat, et al., "Unusual Distributions of Amino Acids in Complementarity-determining (Hypervariable) Segments of Heavy and Light Chains of Immunoglobulins and Their Possible Roles in Specificity of Antibody-combining Sites*", The Journal of Biological Chemistry, Antigenic Determinants/Immunological Specificity, Oct. 10, 1977, pp. 6609-6616, vol. 252, No. 19.
Kabat et al., Sequences of protein of immunological interest. (1991).
Cyrus Chothia, "Canonical Structures for the Hypervariable Regions of Immunoglobulins", Academic Press Limited, J.Mol. Biol., 1987, pp. 901-917, vol. 196.
Robert M. MacCallum, et al., "Antibody-antigen Interactions: Contact Analysis and Binding Site Topography", J. Mol. Biol., 1996, pp. 732-745, vol. 262.
Shigeomi Shimizu, et al., "Induction of Apoptosis as well as Necrosis by Hypoxia and Predominant Prevention of Apoptosis by Bcl-2 and Bcl-X," Cancer Res (1996) 56 (9): 2161-2166.
Hye-Mi Ahn, et al., "Anti-cancer Activity of Novel TM4SF5-Targeting Antibodies through TM4SF5 Neutralization and Immune Cell-Mediated Cytotoxicity", Theranostics, 2017, pp. 594-613, vol. 7, Issue 3.
Doohyung Lee, et al., "Interaction of Tetraspan(in) TM4SF5 With CD44 Promotes Self-Renewal and Circulating Capacities of Hepatocarvinoma Cells", Heptatology, Official Journal of the American Association for the Study of Liver Diseases, 2015, pp. 1978-1997, vol. 61, No. 6.

(Continued)

*Primary Examiner* — Brad Duffy
*Assistant Examiner* — Amber K Faust
(74) *Attorney, Agent, or Firm* — Sughrue Mion, PLLC

(57) ABSTRACT

The present disclosure relates to TM4SF5-specific humanized antibodies and uses thereof.

12 Claims, 27 Drawing Sheets
Specification includes a Sequence Listing.

(56) References Cited

OTHER PUBLICATIONS

Aruljothi Subramaniam, et al., "Potential role of signal transducer and activator of transcription (STAT)3 signaling pathway in inflammation, survival, proliferation and invasion of hepatocellular carcinoma", Elsevier, Biochimica et Biophysica Acta, 2013, pp. 46-60, vol. 1835.
Cho-Rok Jung et al., E2-EPF UCP targets pVHL for degradation and associates with tumor growth and metastasis, Nature Medicine, Jul. 2006, pp. 809-816, vol. 12, No. 7.
Hye Young Yang, et al., "Construction of a Large Synthetic Human scFv Library with Six Diversified CDRs and High Functional Diversity", Springer, Molecules and Cells, Feb. 28, 2009, pp. 225-235, vol. 27.

\* cited by examiner

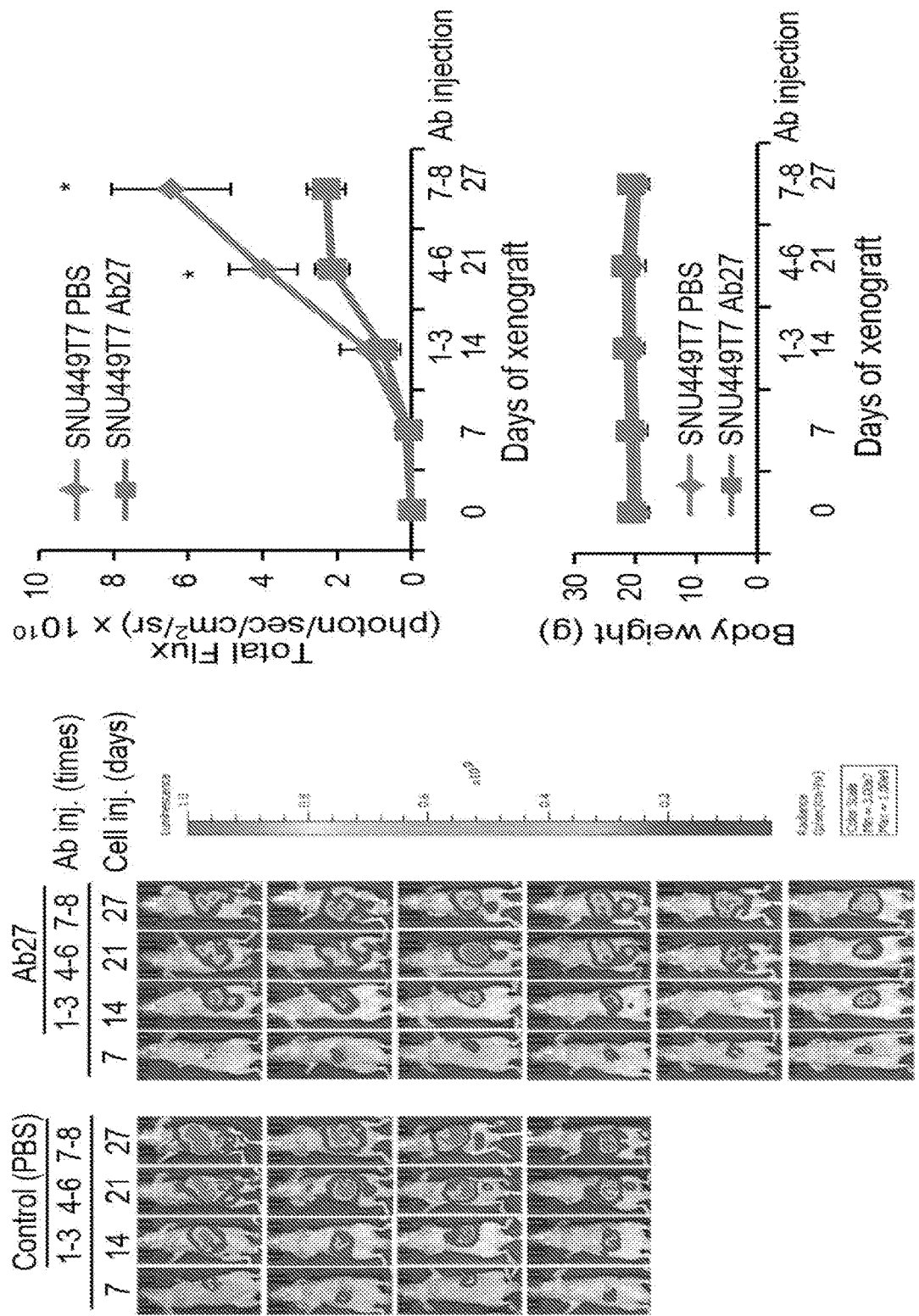
[FIG. 1a]

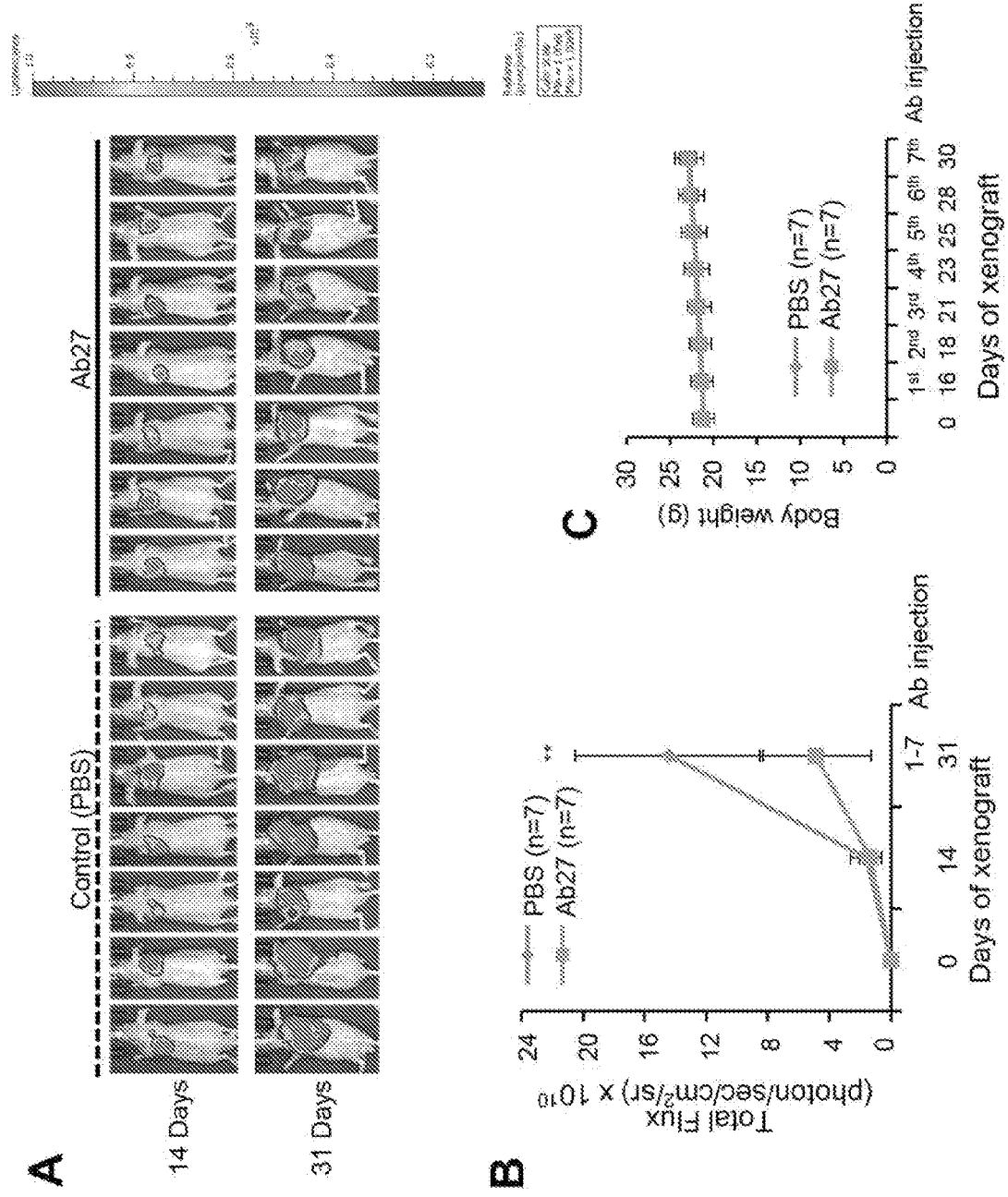
[FIG. 1b]

[FIG. 2]
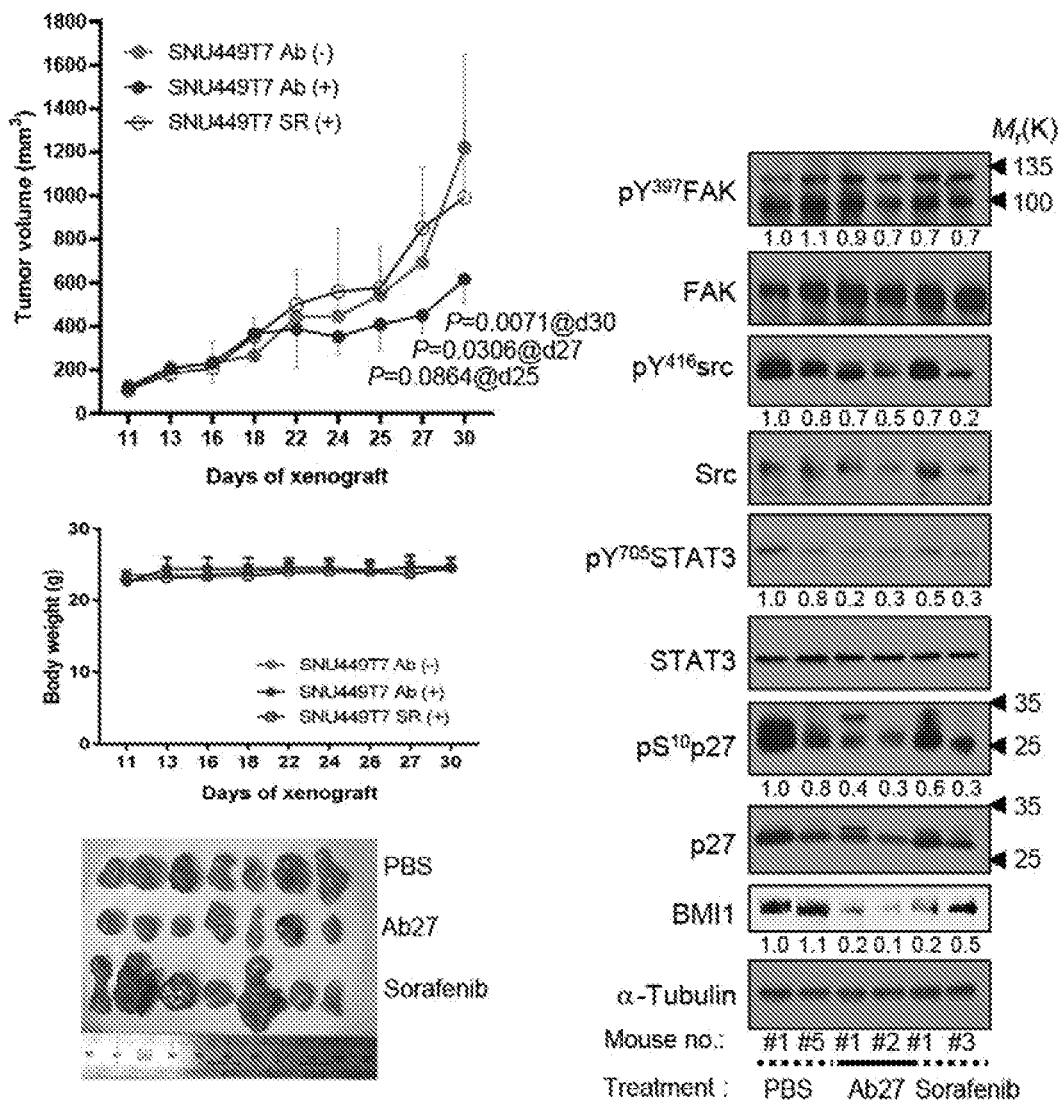

[FIG. 3]
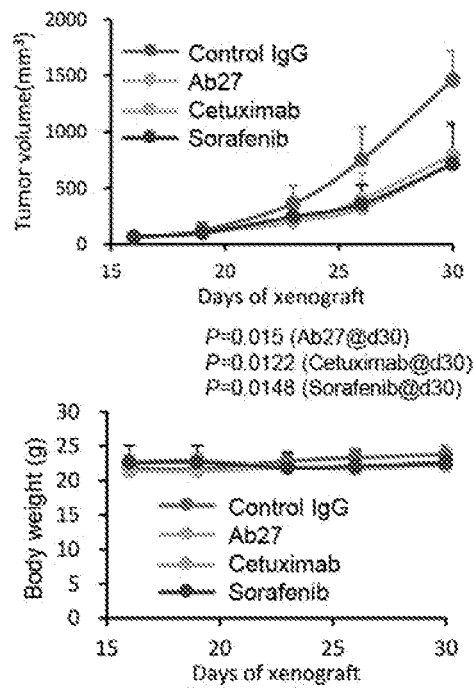
[FIG. 4]
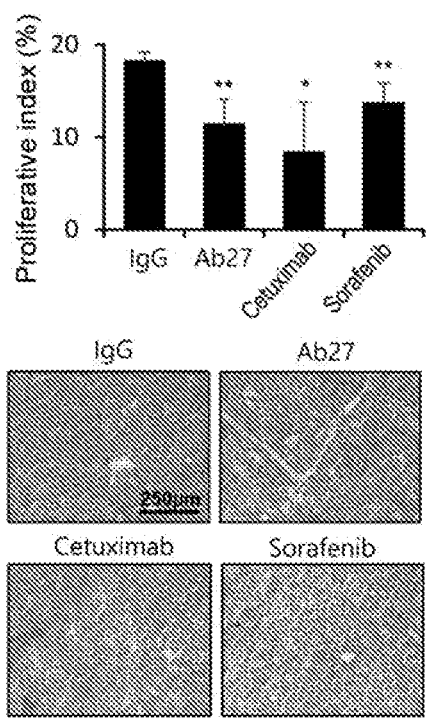

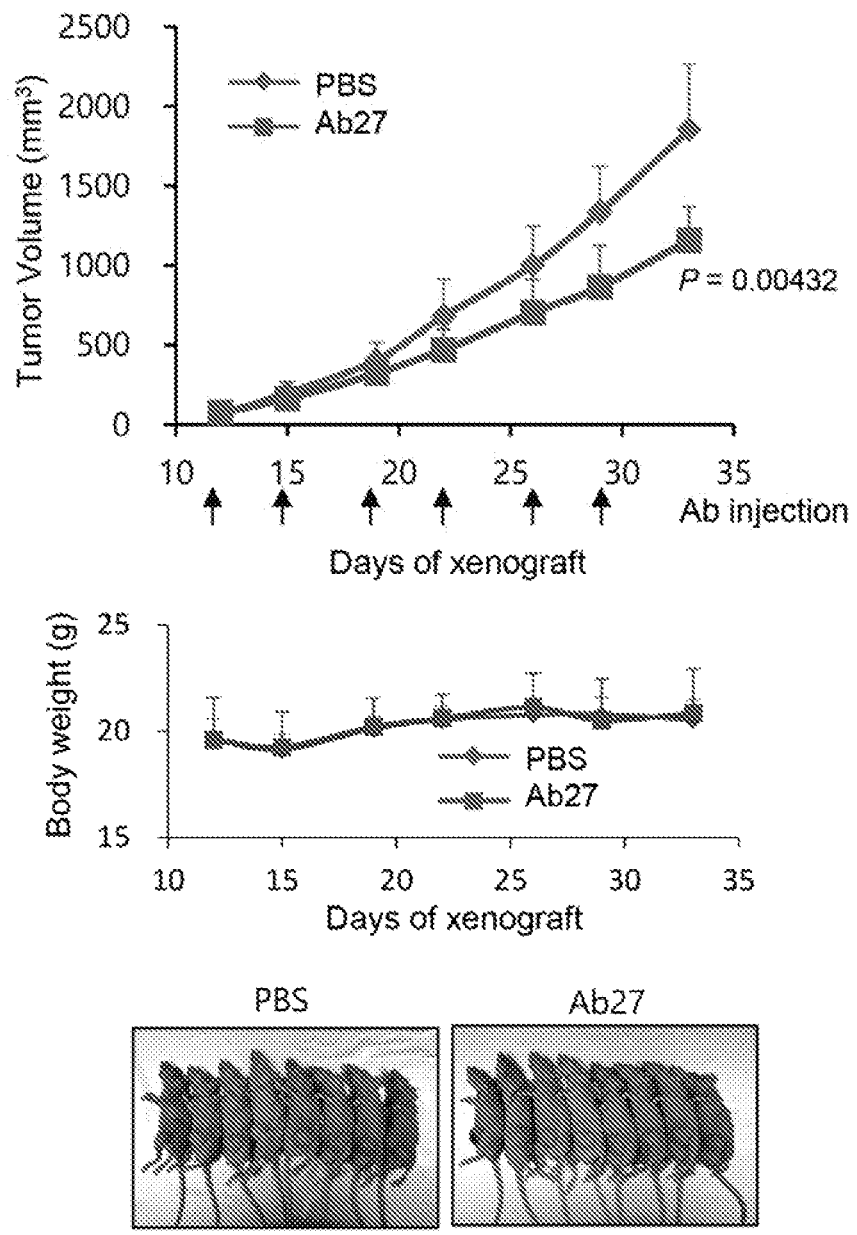
[FIG. 5]

[FIG. 6]
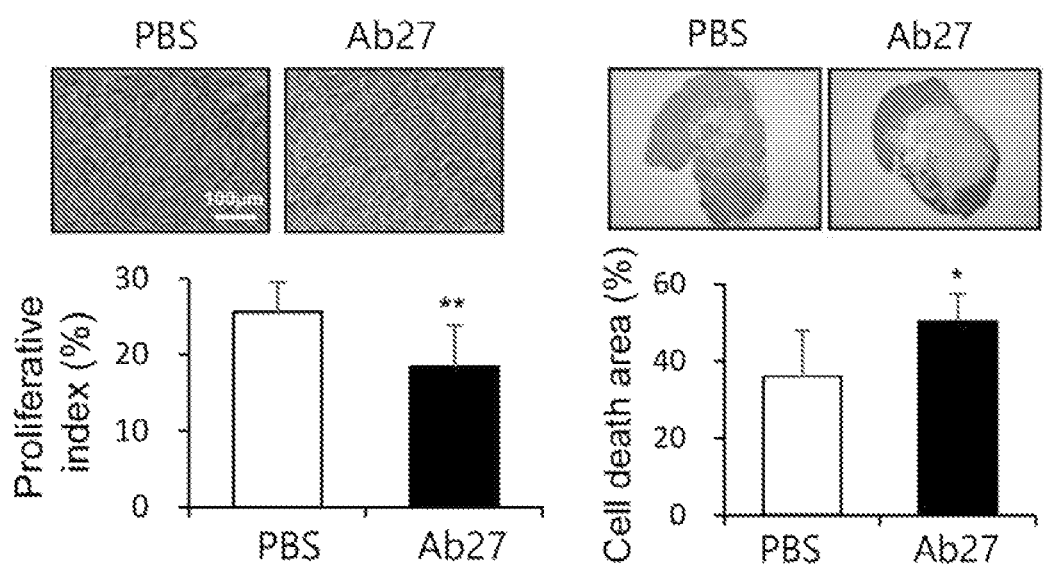

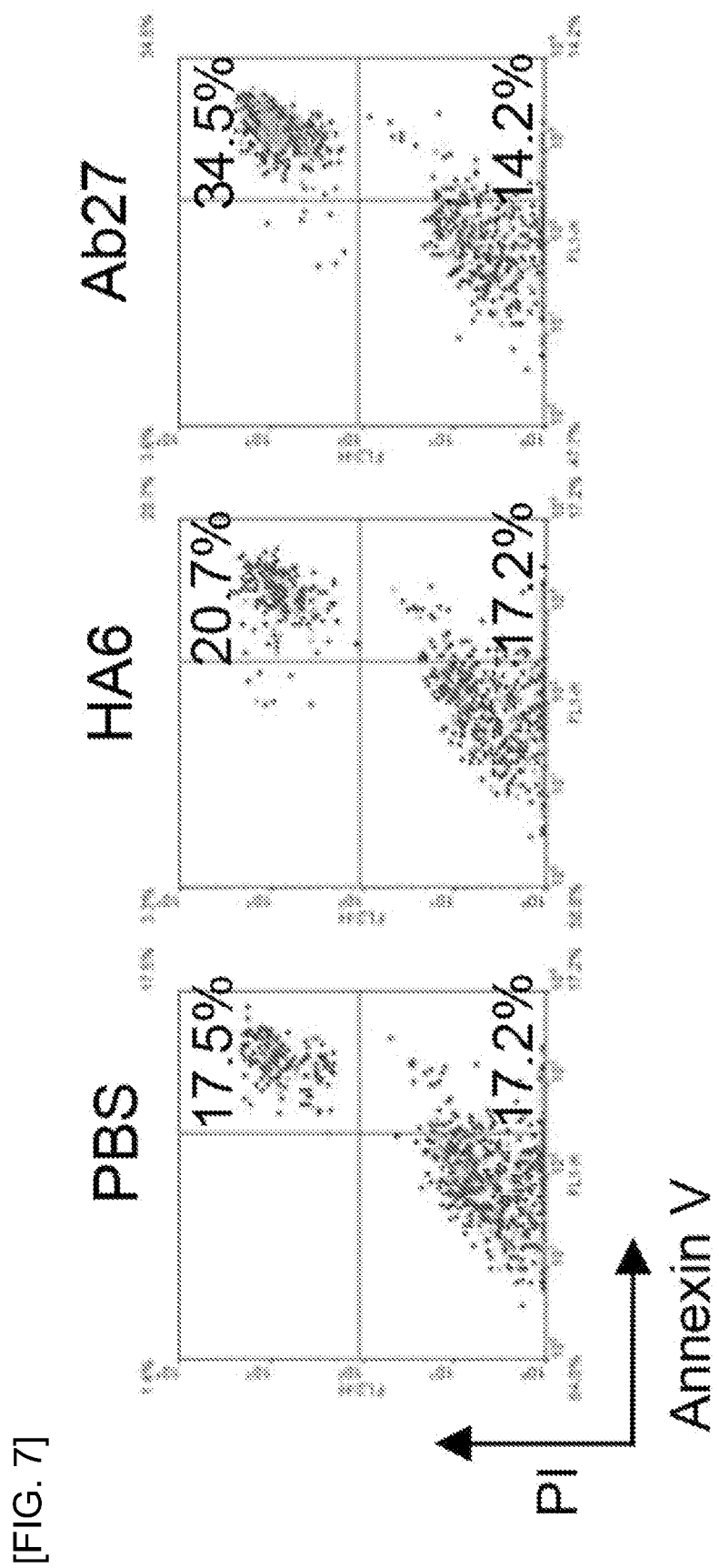
[FIG. 7]

[FIG. 8]
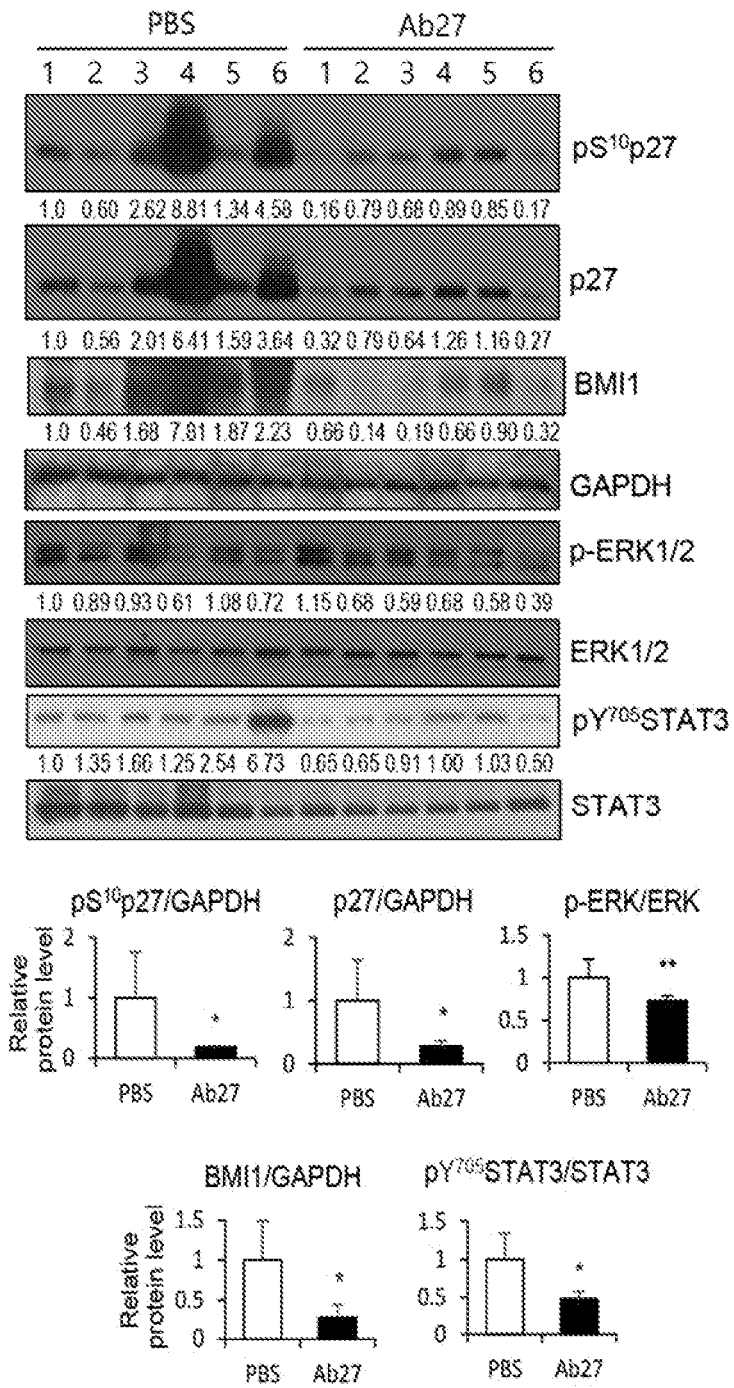

[FIG. 9]
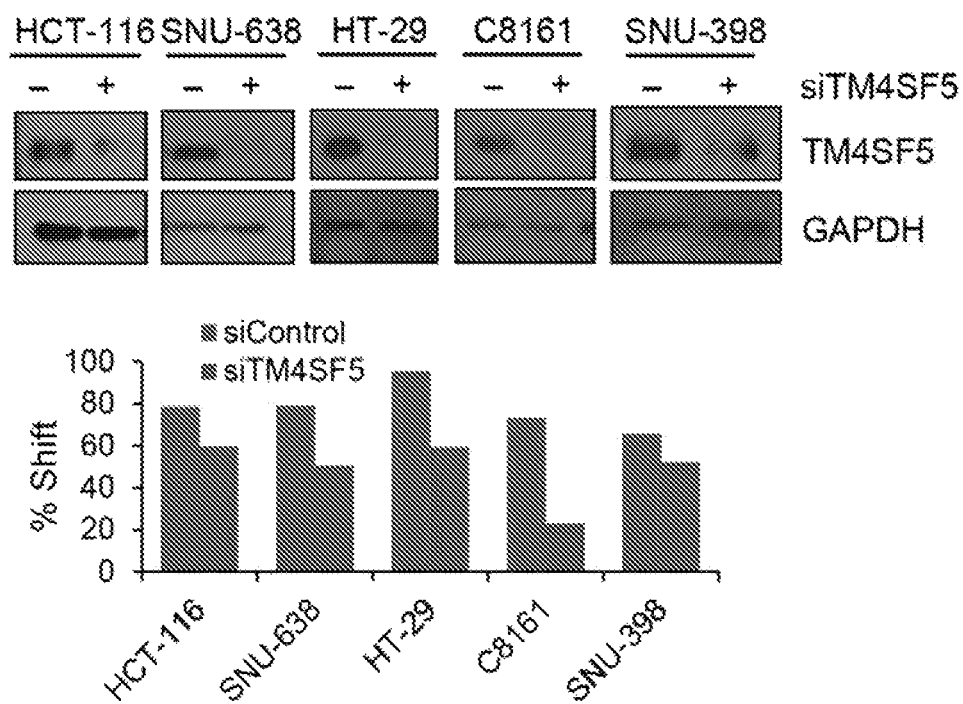

[FIG. 10]
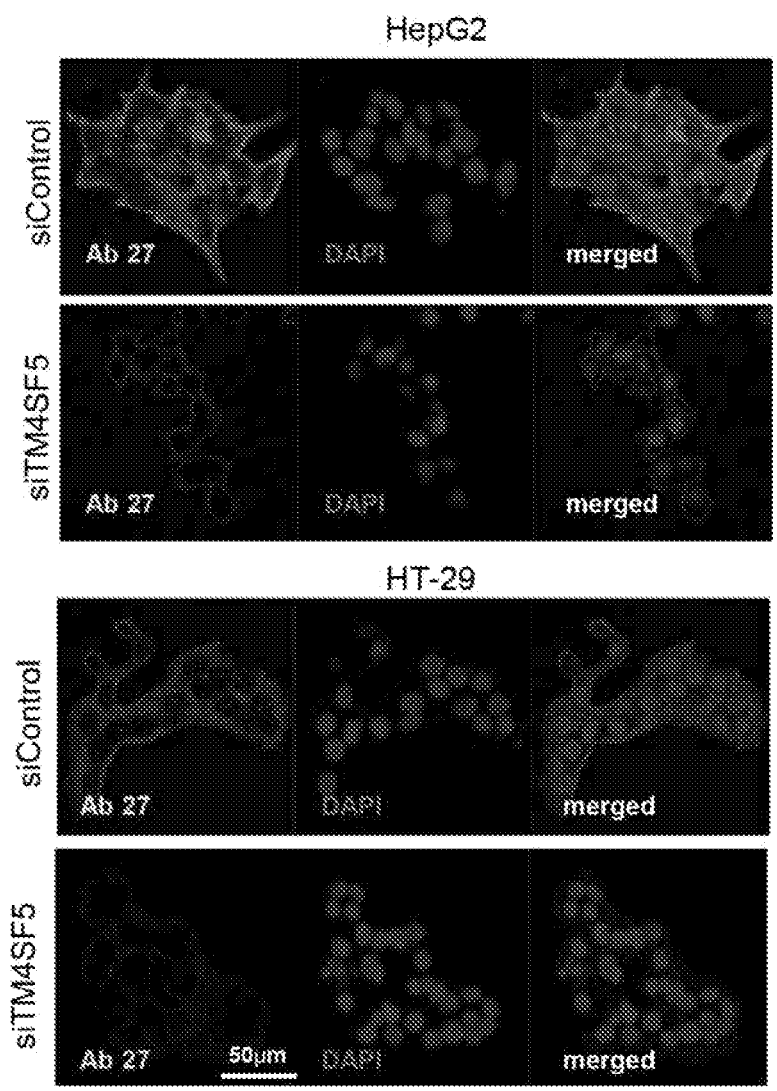

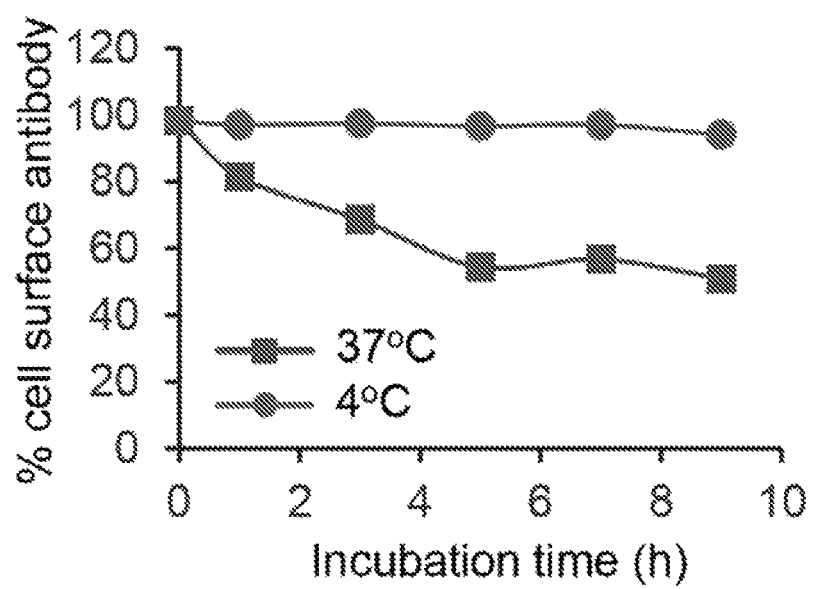
[FIG. 11]

[FIG. 12]
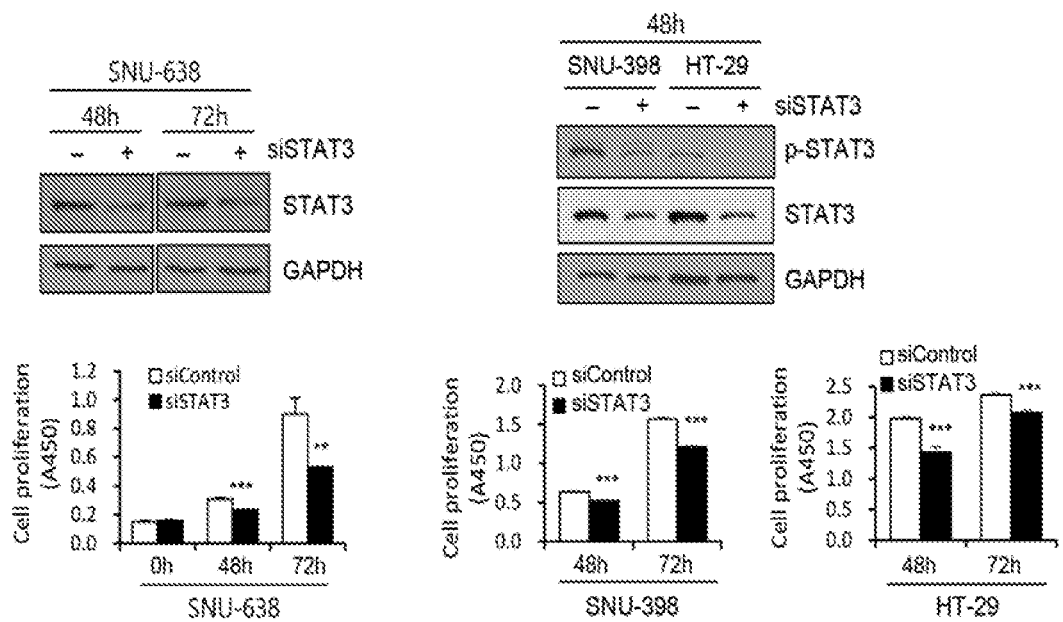
[FIG. 13]
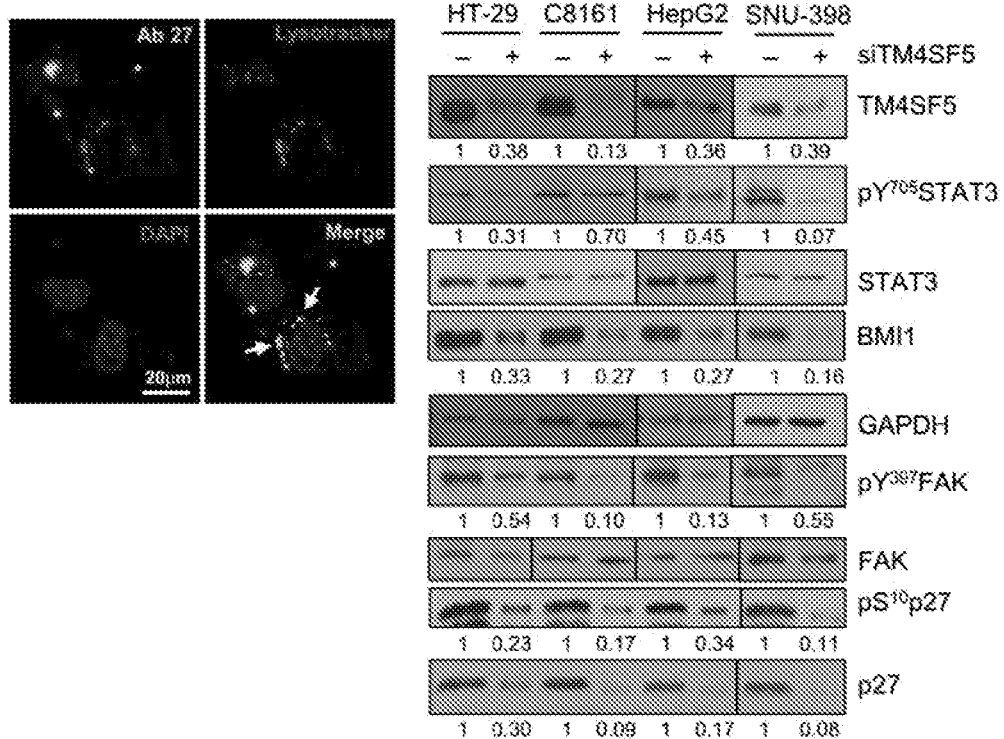

[FIG. 14]
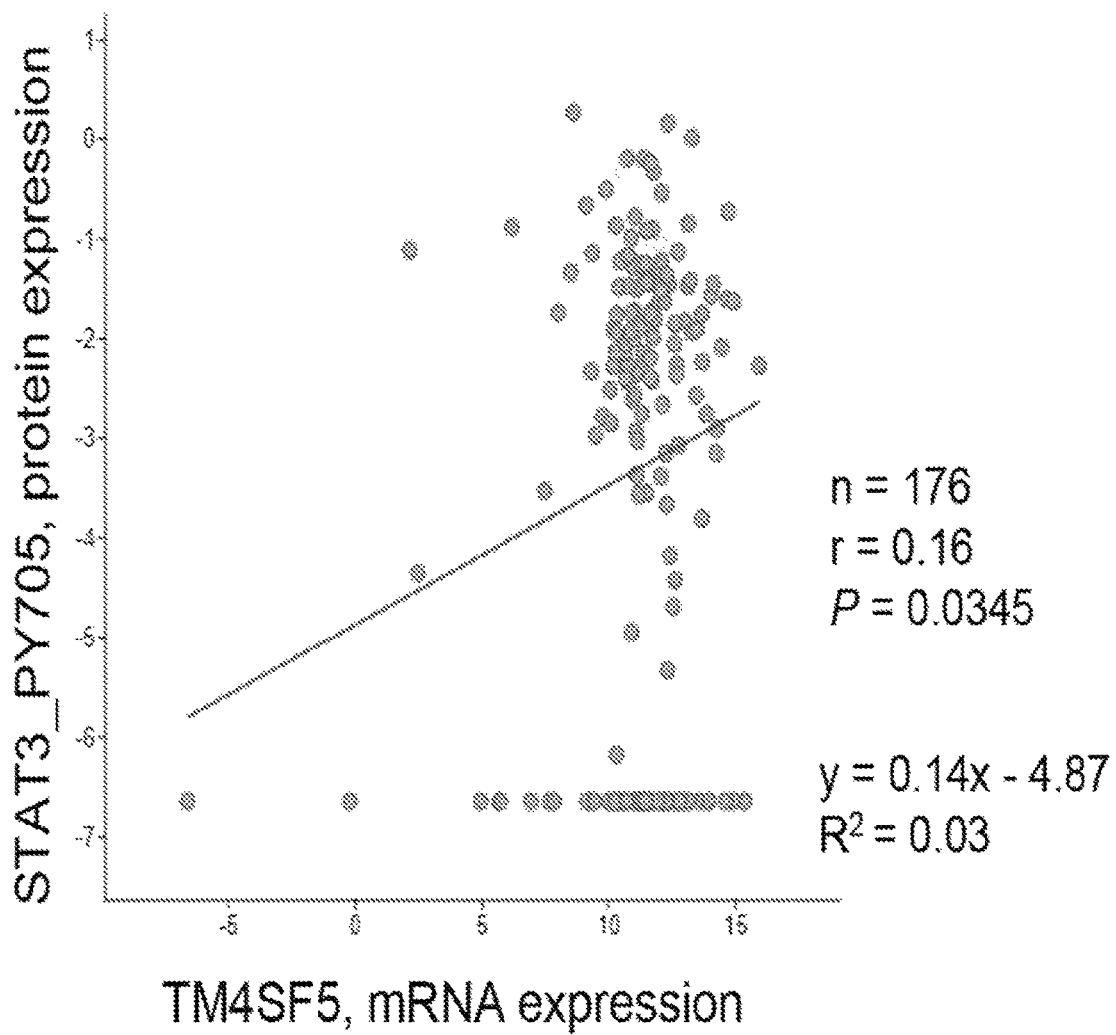

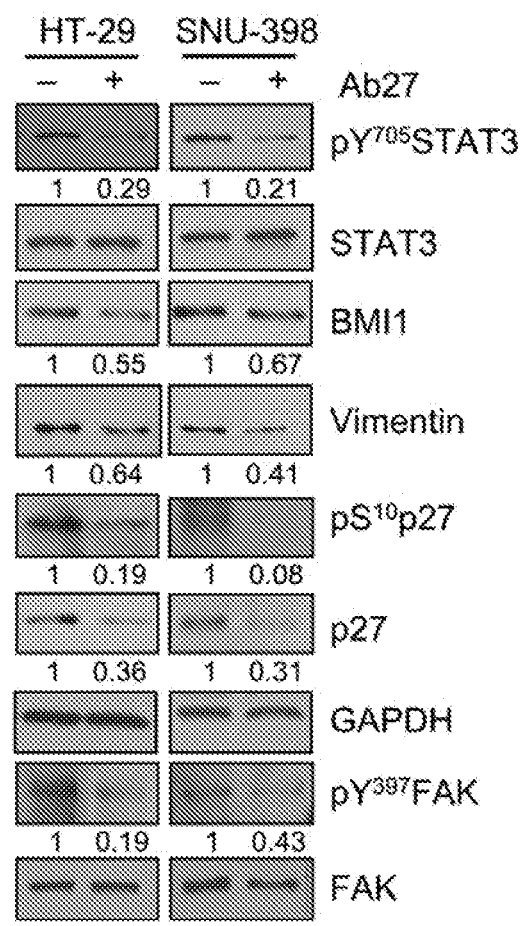
[FIG. 15a]

[FIG. 15b]
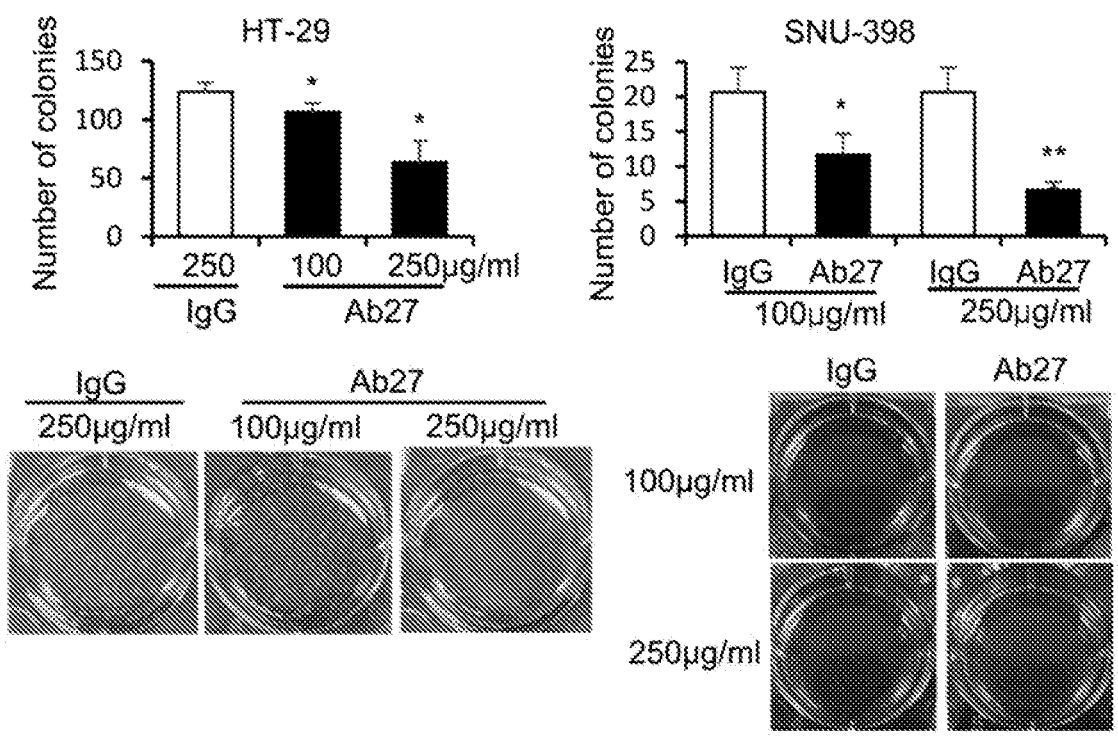

[FIG. 16]
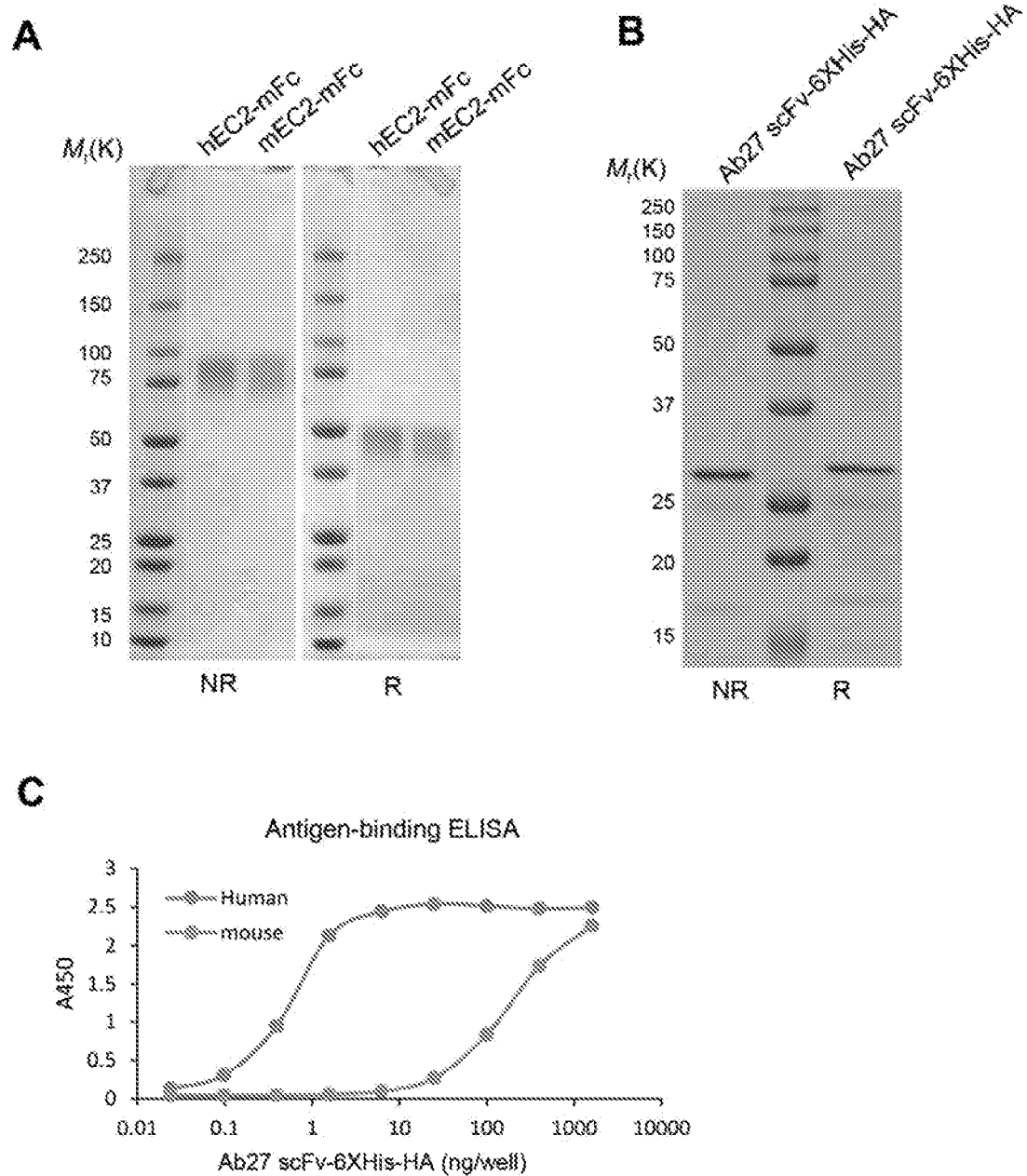

[FIG. 17]
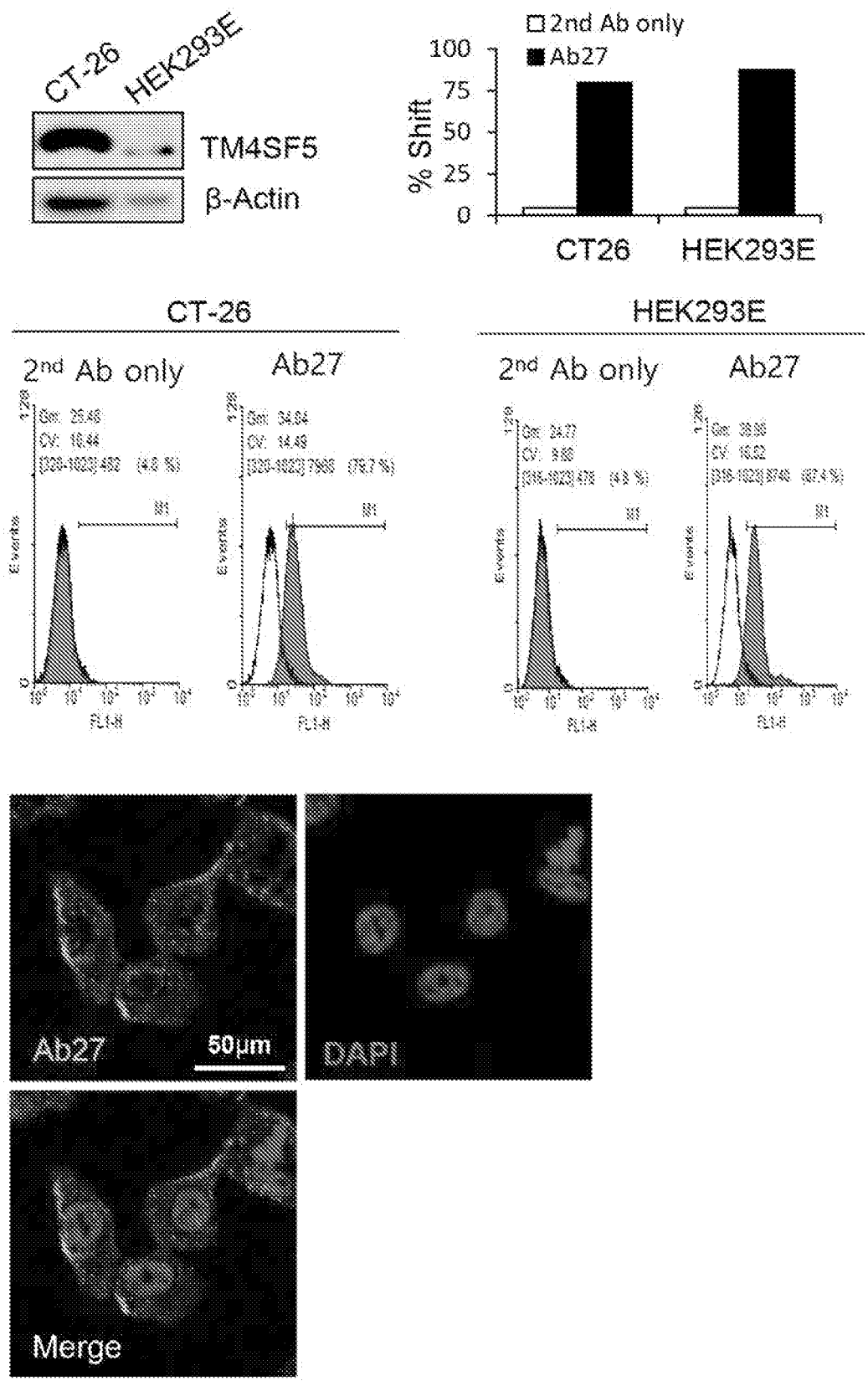

[FIG. 18]
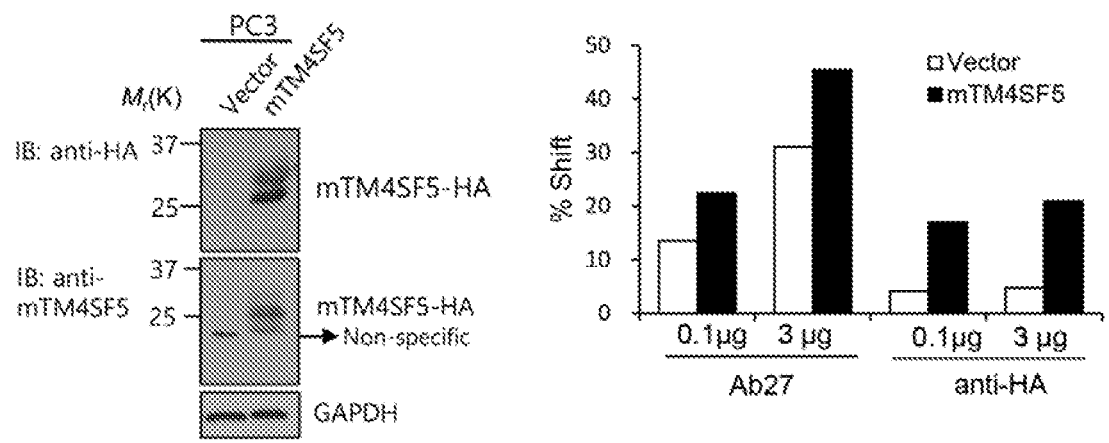
[FIG. 19]
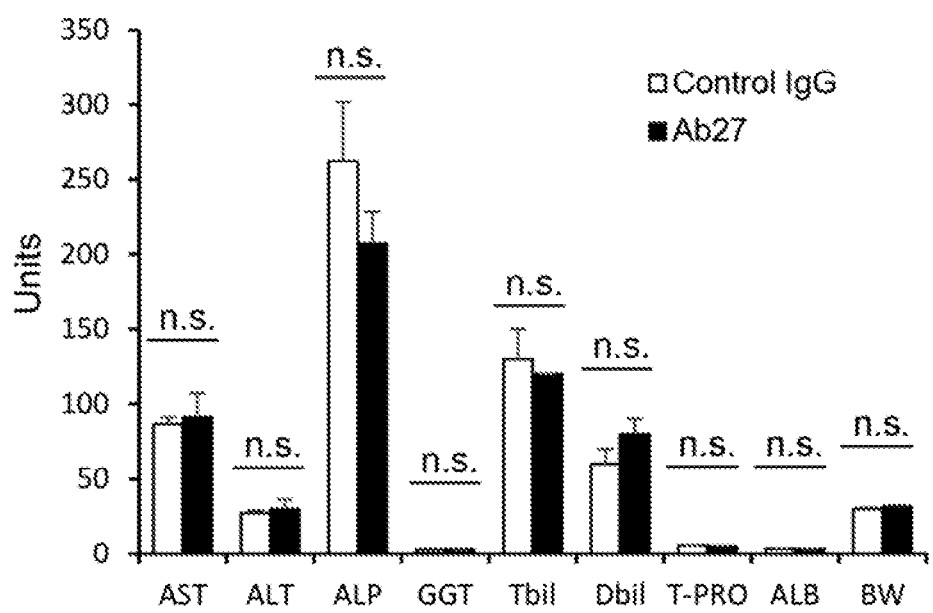

[FIG. 20]
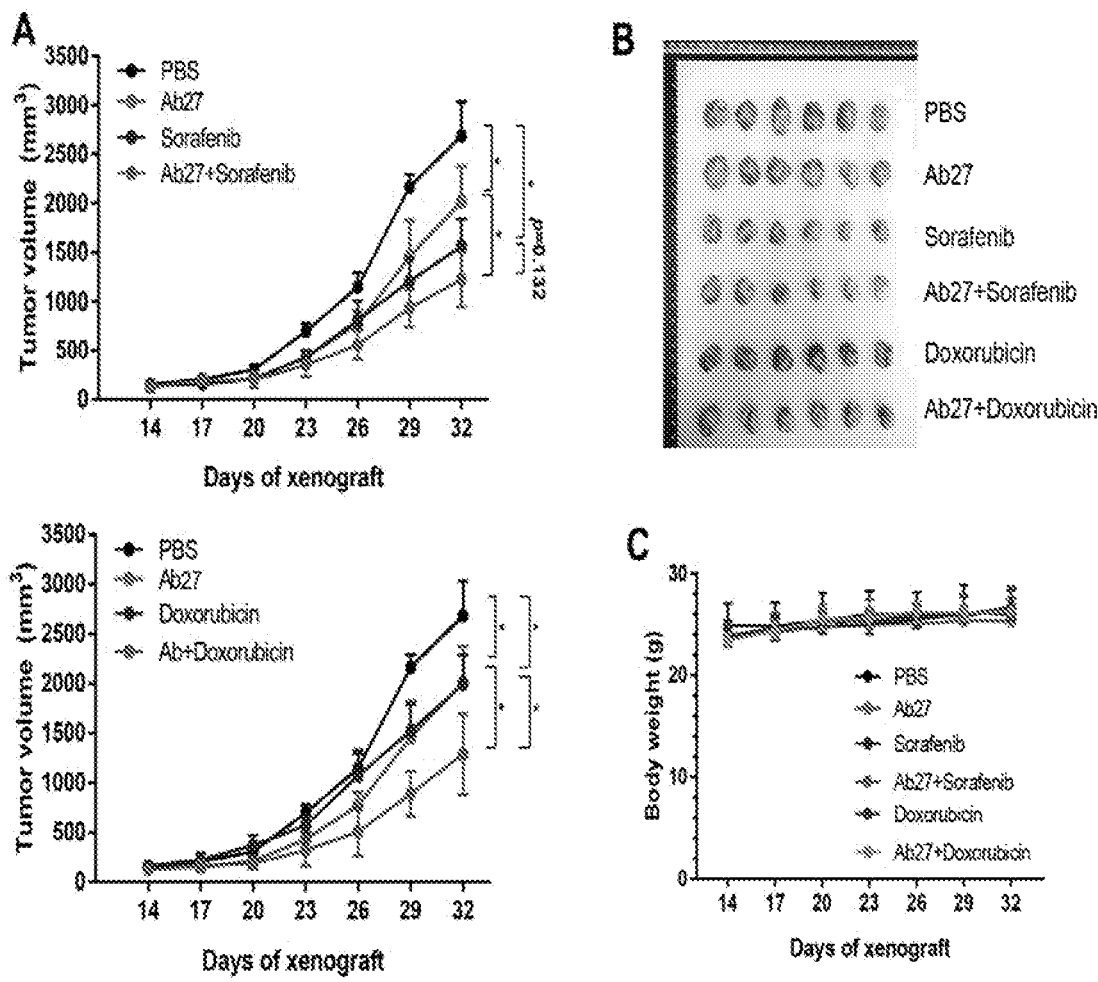

[FIG. 21]

[FIG. 22a]
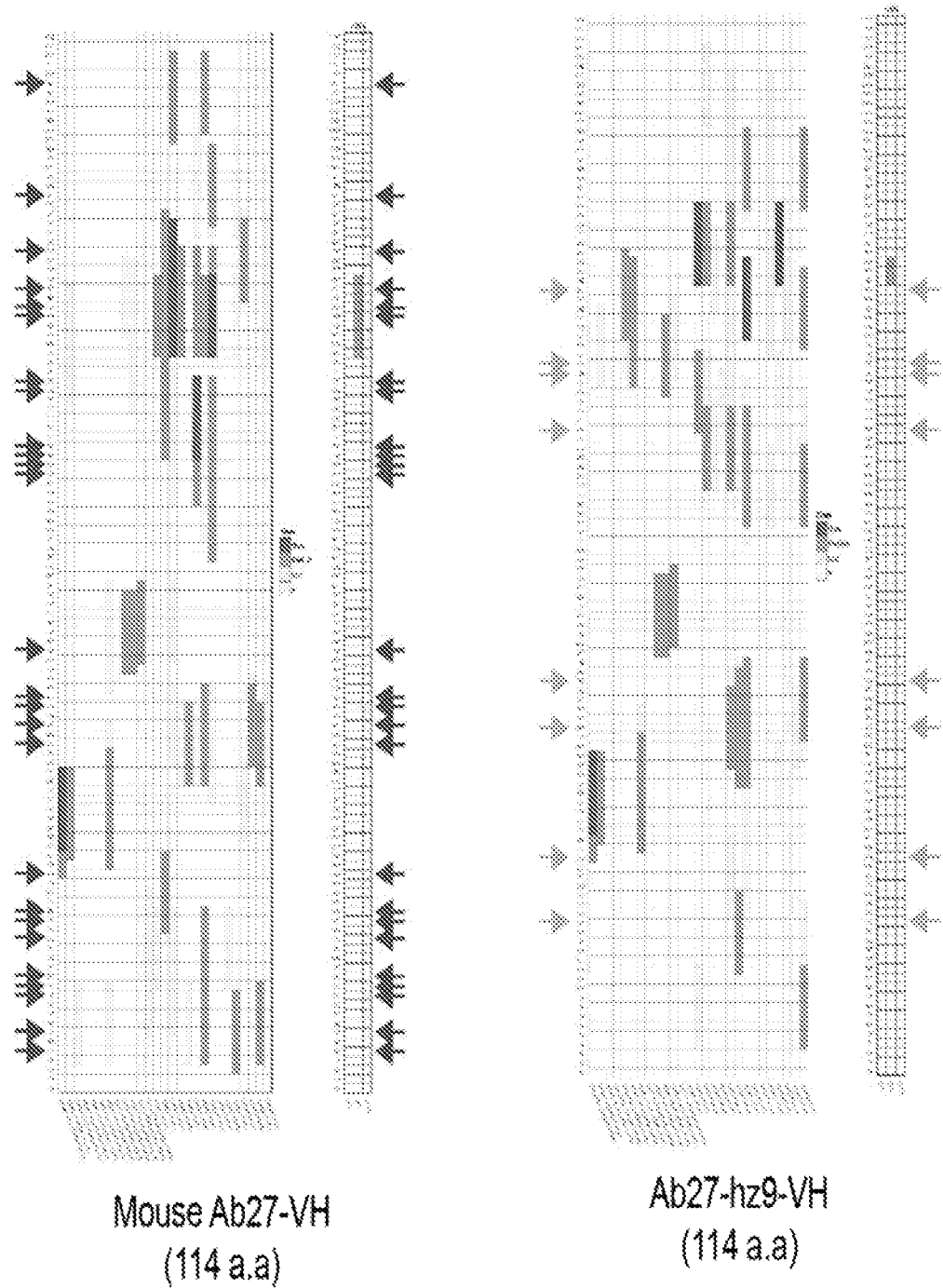

[FIG. 22b]
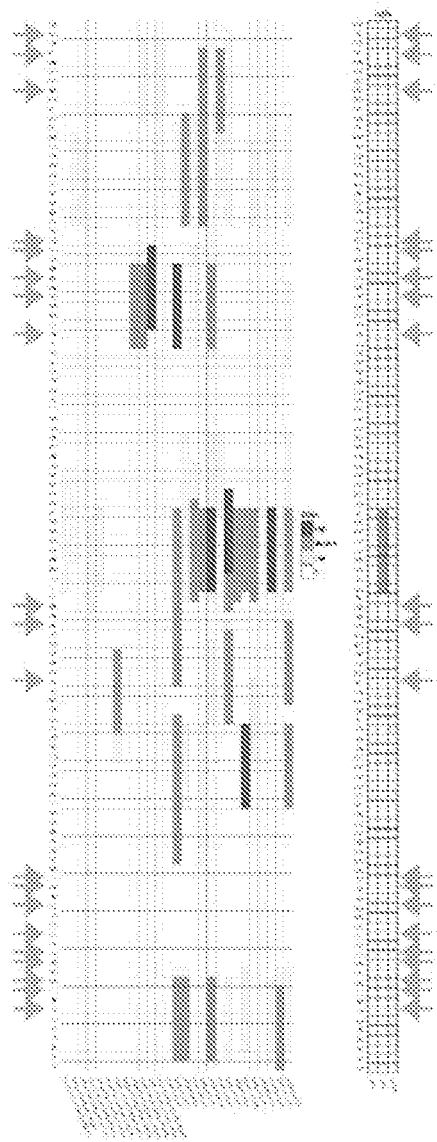
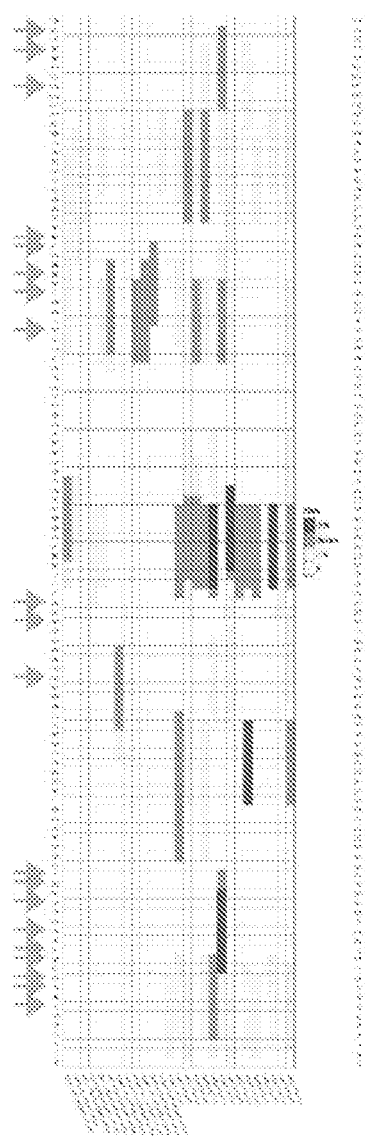
Mouse Ab27-VL (112 a.a)     Ab27-hz9-VL (112 a.a)

[FIG. 22c]
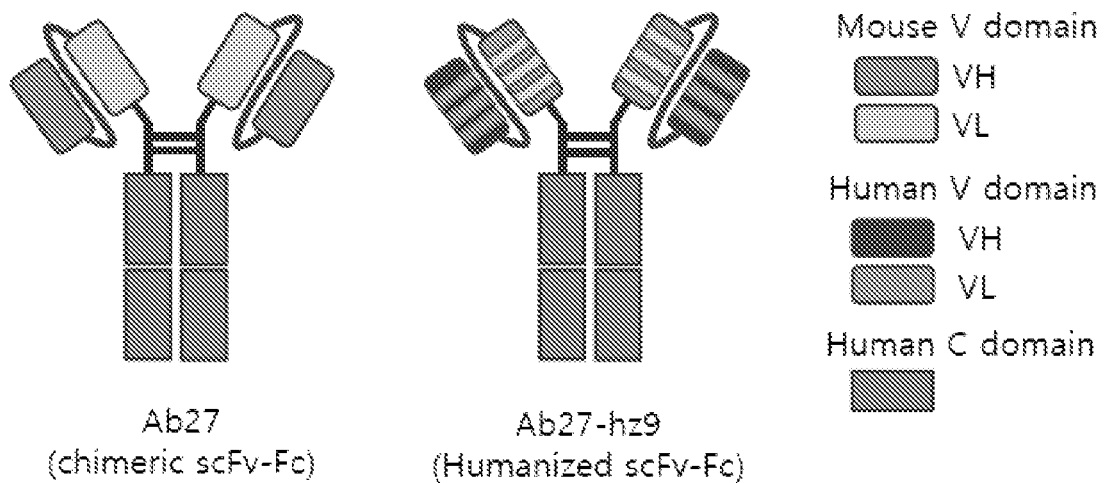

[FIG. 23]
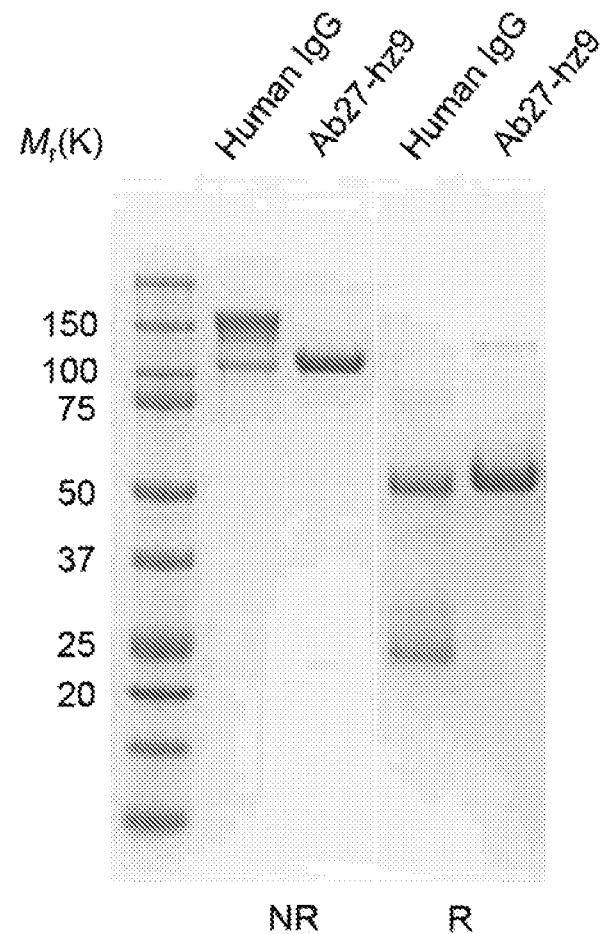
[FIG. 24]
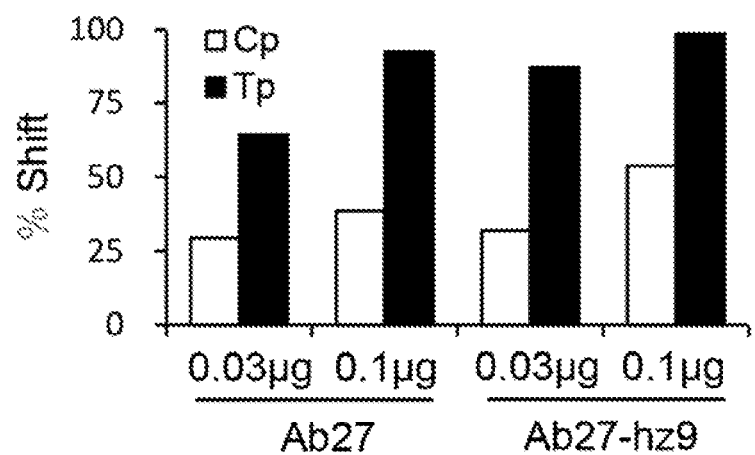

[FIG. 25]
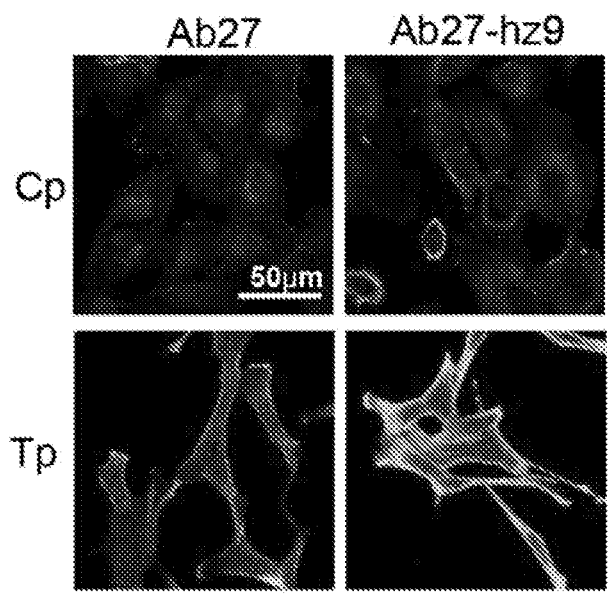
[FIG. 26]
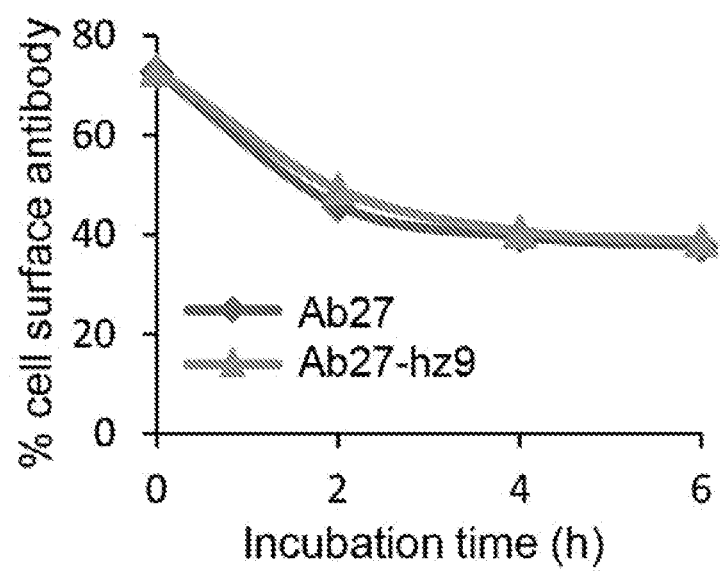

[FIG. 27]
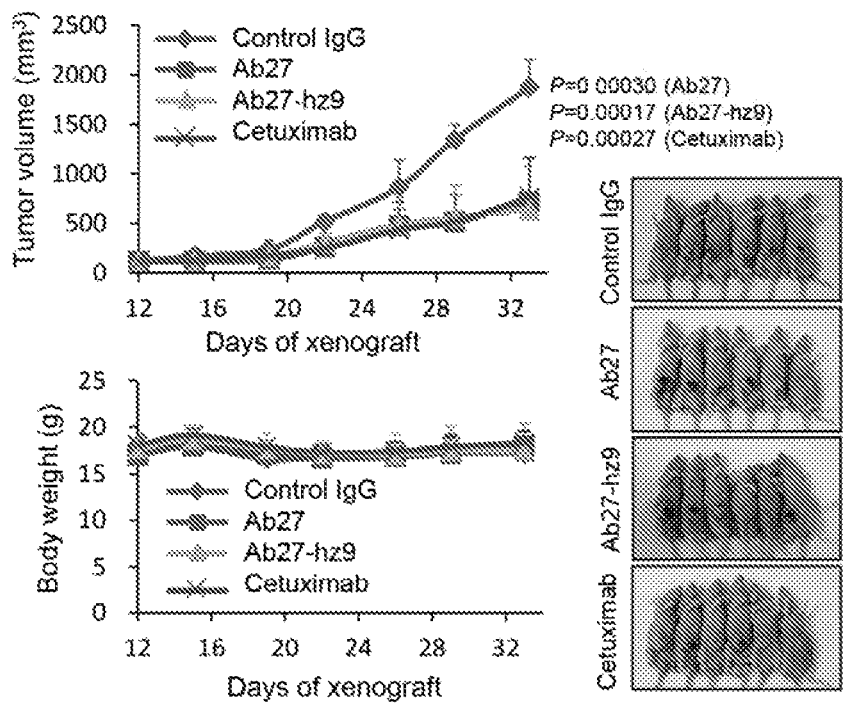
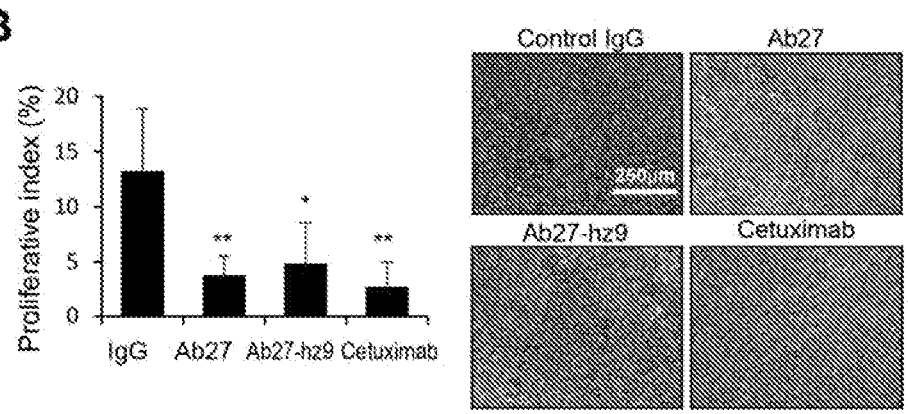

[FIG. 28]
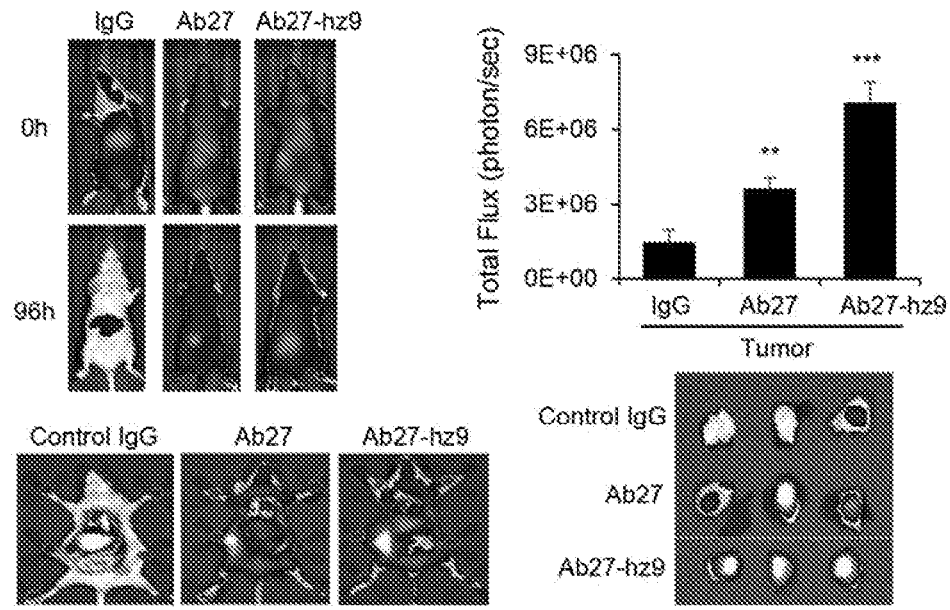
[FIG. 29]
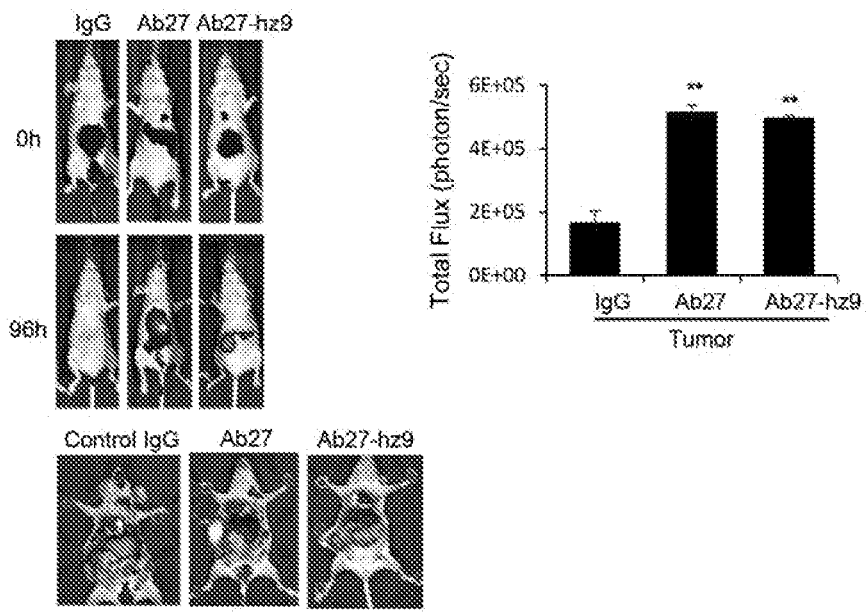

TM4SF5-TARGETING HUMANIZED ANTIBODY AND USE THEREOF

CROSS-REFERENCE TO RELATED APPLICATION

This application claims priority from Korean Patent Application No. 10-2022-0005907 filed Jan. 14, 2022, the disclosure of which is incorporated herein by reference in its entirety.

SEQUENCE LISTING

The content of the electronically submitted sequence listing, file name: Q284226_XML sequence listing.XML; size: 11,518 bytes; and date of creation: Jan. 12, 2023, is hereby incorporated by reference in their entirety.

TECHNICAL FIELD

The present disclosure relates to TM4SF5-targeting humanized antibodies and uses thereof.

BACKGROUND ART

Transmembrane 4 superfamily (TM4SF) proteins are a group of hydrophobic proteins having a molecular weight of about 25-50 kDa including four transmembrane domains, two extracellular loops, and two short cytoplasmic tail regions, which are also called tetraspanin or tetraspan. The TM4SF proteins form a complex on the cell membrane along with cell adhesion molecules (e.g., integrin), thereby establishing a gigantic tetraspanin-enriched microdomain (TERM) and contributing to various biological functions (e.g., cell adhesion, proliferation, differentiation, metabolic control, interactions with immune system, and migration).

TM4SF5, which refers to transmembrane 4 L6 family member 5 or four-transmembrane L6 superfamily member 5, is a member of the tetraspanin family, and has a structure including four domains of non-soluble proteins which penetrate through cell membranes, with two loops present extracellularly, and one loop and two tails present in the cytoplasm. TM4SF5 is a homologue of the tumor-associated antigen L6 (TM4SF1), and mRNA of TM4SF1 is known to be highly overexpressed in pancreatic cancer, stomach cancer, liver cancer, colorectal cancer, soft tissue sarcoma, etc. Additionally, artificial expression of a TM4SF5 protein in COS7 cells resulted in actin reorganization and focal adhesion turnover, thus suggesting that TM4SF5 may be involved in cell migration through epithelial—mesenchymal transition (EMT) (Lee S. A. et al., *J Clin Invest* 2008, 118(4):1354-66). Additionally, TM4SF5 proteins, due to their high amino acid sequence homology to L6 (i.e., a cancer-related gene), have been suspected as being encoded by a cancer-related gene, and have been reported to be associated with development and progression of cancer. TM4SF5 is involved in cell proliferation by promoting the progression of G1/S cycle through the intracellular expression of p27Kip1 and the activity of RhoA GTPase (Kim H. et al., *Biochim Biophys Acta* 2010 1803(8):975-82), and the cross-talk in the signaling pathway between transforming growth factor-β1 (TGF-β1) and epidermal growth factor receptor (EGFR) involved in EMT is known to induce the expression of TM4SF5, thereby bringing about EMT (Kang M. et al., *Biochem J* 2012 443(3):691-700).

As described above, with the emerging importance of TM4SF5 as a specific protein and anticancer target for a new cancer diagnosis, studies have been focused on diagnosing cancer having the TM4SF5 as a target. Additionally, for cancer treatment with TM4SF5 as a target, studies have been focused on the inhibition of the biological activities of TM4SF5 in various fields. In particular, studies have been focused on the compounds that can inhibit the activities of TM4SF5, for example, sulfonamide- and sulfonate-substituted chalcone derivatives have been reported to inhibit the biological activities of TM4SF5 (KR Patent No. 10-0934706). In addition to the compounds inhibiting the biological activities of TM4SF5 described above, there has been a growing need for the development of antibody therapeutics that specifically bind to TM4SF5.

As a result, the present inventors have succeeded in developing a humanized antibody that specifically binds to a human TM4SF5 protein, thereby completing the present disclosure.

DISCLOSURE

Technical Problem

An object of the present disclosure is to provide an antibody or antigen-binding fragment thereof that binds to TM4SF5.

Another object of the present disclosure is to provide a pharmaceutical composition for preventing or treating TM4SF5-related diseases comprising the antibody or antigen-binding fragment thereof.

Still another object of the present disclosure is to provide a composition for diagnosing TM4SF5-related diseases comprising the antibody or antigen-binding fragment thereof.

Still another object of the present disclosure is to provide a polynucleotide encoding the antibody or antigen-binding fragment thereof; and a transformant comprising the polynucleotide.

Technical Solution

An aspect of the present disclosure provides an antibody or antigen-binding fragment thereof that binds to TM4SF5. In an embodiment, the antibody or antigen binding fragment thereof is characterized in that it comprises:
- a heavy chain variable domain comprising HCDR1 represented by SEQ ID NO: 9; HCDR2 represented by SEQ ID NO: 10; and HCDR3 represented by SEQ ID NO: 3; and
- a light chain variable domain comprising LCDR1 represented by SEQ ID NO: 4; LCDR2 represented by SEQ ID NO: 5; and LCDR3 represented by SEQ ID NO: 6.

In another embodiment, the antibody or antigen binding fragment thereof is characterized in that it comprises:
- a heavy chain variable domain comprising HCDR1 represented by SEQ ID NO: 1; HCDR2 represented by SEQ ID NO: 2; and HCDR3 represented by SEQ ID NO: 3; and
- a light chain variable domain comprising LCDR1 represented by SEQ ID NO: 4; LCDR2 represented by SEQ ID NO: 5; and LCDR3 represented by SEQ ID NO: 6.

In the antibody or antigen binding fragment thereof according to any one of previous embodiments, the CDR sequences of SEQ ID NOS: 9 and 10 are assigned according to the numbering system of Chothia.

In the antibody or antigen binding fragment thereof according to any one of previous embodiments, the CDR sequences of SEQ ID NOS: 1 and 2 are assigned according to the numbering system of Kabat.

The antibody or antigen binding fragment thereof according to any one of previous embodiments is characterized in that it comprises a heavy chain variable domain represented by SEQ ID NO: 7.

The antibody or antigen binding fragment thereof according to any one of previous embodiments is characterized in that it comprises a light chain variable domain represented by SEQ ID NO: 8.

The antibody according to any one of the previous embodiments is characterized in that it is an IgG antibody.

In the antibody or antigen binding fragment thereof according to any one of previous embodiments is characterized in that it is selected from the group consisting of Fab fragments, Fab' fragments, F'(ab)$_2$ fragments, Fd fragments, Fv fragments, single chain antibodies, diabodies, biparatopic peptides, domain antibodies (dAbs), CDR-grafted antibodies, single chain antibodies (scFv), single chain antibody fragments, diabodies, triabodies, tetrabodies, minibodies, linear antibodies, chelated recombinant antibodies, tribodies, bibodies, intrabodies, nanobodies, small modular immunopharmaceuticals (SMIPs), antigen binding domain immunoglobulin fusion proteins, single domain antibodies, and antibodies containing VHH.

Another aspect of the present disclosure provides a pharmaceutical composition for preventing or treating TM4SF5-related diseases comprising an antibody or an antigen-binding fragment thereof that binds to TM4SF5.

In a specific embodiment, the TM4SF5-related diseases are selected from the group consisting of fatty liver, steatohepatitis, liver fibrosis, liver cirrhosis, portal hypertension, liver cancer, stomach cancer, colorectal cancer, rectal cancer, oral cancer, pharynx cancer, larynx cancer, lung cancer, colon cancer, breast cancer, cervical cancer, endometrial cancer, ovarian cancer, prostate cancer, testicular cancer, bladder cancer, kidney cancer, pancreatic cancer, bone cancer, connective tissue cancer, skin cancer, brain cancer, thyroid cancer, leukemia, Hodgkin's disease, soft tissue sarcoma, lymphoma, multiple myeloma, and blood cancer.

In another specific embodiment, the TM4SF5-related diseases are selected from the group consisting of fatty liver, steatohepatitis, liver fibrosis, liver cirrhosis, portal hypertension, liver cancer, stomach cancer, colorectal cancer, colon cancer, prostate cancer, pancreatic cancer, and soft tissue sarcoma.

The pharmaceutical composition according to any one of the previous embodiments is characterized in that it is administered along with any one material selected from the group consisting of 5-fluorouracil (5-FU), oxaliplatin, doxorubicin, sorafenib, and cetuximab.

Still another aspect of the present disclosure provides a method for preventing or treating TM4SF5-related diseases, which includes administering an antibody or antigen-binding fragment thereof that binds to TM4SF5 to a subject.

Still another aspect of the present disclosure provides a polynucleotide, which encodes the antibody or antigen-binding fragment thereof that binds to TM4SF5.

Still another aspect of the present disclosure provides an expression vector, which includes the polynucleotide encoding the antibody or antigen-binding fragment thereof that binds to TM4SF5.

Still another aspect of the present disclosure provides a transformant, which includes a polynucleotide that encodes the antibody or antigen-binding fragment thereof that binds to TM4SF5; or an expression vector including the same.

Still another aspect of the present disclosure provides a composition for diagnosing TM4SF5-related diseases, which includes the antibody or antigen-binding fragment thereof that binds to TM4SF5.

Still another aspect of the present disclosure provides a method for providing information for the diagnosis of TM4SF5-related diseases, which includes detecting transmembrane 4 L6 family member 5 (TM4SF5) protein in a biological sample through an antigen-antibody reaction using an antibody or antigen-binding fragment thereof that binds to TM4SF5.

The present disclosure is described in detail as follows. Meanwhile, respective descriptions and embodiments disclosed in the present disclosure may also be applied to other descriptions and embodiments. That is, all combinations of various elements disclosed in the present disclosure fall within the scope of the present disclosure. Further, the scope of the present disclosure is not limited by the specific description below.

Additionally, those skilled in the art will be able to recognize or confirm, based on routine experimentation, many equivalents to the specific embodiments of the present disclosure described in this application, and such equivalents are intended to be included in the present disclosure.

Additionally, a number of literature references and patent documents are referenced throughout this specification and their citations are indicated. The disclosures of the cited literature references and patent documents are incorporated by reference into this specification in their entirety, so that the level of the technical field to which the present disclosure belongs and the content of the present disclosure are more clearly described.

As used herein, the term "antibody" refers to a protein molecule acting as a ligand that specifically recognizes an antigen, including an immunoglobulin molecule immunologically reactive with a specific antigen.

Additionally, the term also includes bispecific molecules (e.g., bispecific antibodies), diabodies, triabodies, and tetrabodies. The whole antibodies have two full-length light chains and two full-length heavy chains, and each of the light chains is linked to a heavy chain by a disulfide bond.

The whole antibodies include IgA, IgD, IgE, IgM, and IgG, and IgG includes IgG1, IgG2, IgG3, and IgG4 as subtypes. In an embodiment, the antibody provided in the present disclosure may be an IgG antibody. As used herein, the terms "antigen-binding fragment" and "antibody fragment" refer to any fragment of an antibody of the present disclosure that retains antigen-binding activity and are used interchangeably.

The antibody or antigen-binding fragment of the present disclosure may be selected from the group consisting of Fab fragments, Fab' fragments, F'(ab)$_2$ fragments, Fd fragments, Fv fragments, single chain antibodies, diabodies, biparatopic peptides, domain antibodies (dAbs), CDR-grafted antibodies, single chain antibodies (scFv), single chain antibody fragments, diabodies, triabodies, tetrabodies, minibodies, linear antibodies, chelated recombinant antibodies, tribodies, bibodies, intrabodies, nanobodies, small modular immunopharmaceuticals (SMIPs), antigen binding domain immunoglobulin fusion proteins, single domain antibodies, and antibodies containing VHH.

The Fd refers to a heavy chain part included in the Fab fragment. The Fab has a structure which includes a variable region of light and heavy chains, a constant region of a light chain (framework region, FR), and the first constant region of a heavy chain (CH1 domain), and it has one antigen-binding site. Fab' is different from Fab in that it has a hinge region including one or more cysteine residues at the C-terminus of the heavy chain CH1 domain. F'(ab)$_2$ antibodies are produced by forming a disulfide bond between cysteine residues in the hinge region of Fab'.

Fv (variable fragment) refers to a minimum antibody fragment having only a heavy chain variable region and a light chain variable region. A double chain Fv (dsFv) has a structure where a heavy chain variable region and a light chain variable region are linked by a disulfide bond, and a single chain Fv (scFv) generally has a structure where a heavy chain variable region and a light chain variable region are covalently linked through a peptide linker. These antibody fragments can be obtained using a protease (e.g., Fab fragments can be obtained by cleaving the whole antibody with papain, whereas F(ab')2 fragments can be obtained by cleaving the whole antibody with pepsin), for example, through genetic recombination technology.

In the present disclosure, the variable region of a heavy chain may be named "VH"; the variable region of a light chain may be named "LH"; the CDR of a heavy chain may each be named "VH-CDR1", "VH-CDR2", and "VH-CDR3"; the CDR of a light chain may each be named "VL-CDR1", "VL-CDR2", and "VL-CDR3"; the FR of a heavy chain may each be named "VH-FR1", "VH-FR2", "VH-FR3", and "VH-FR4"; and the FR of a light chain may each be named "VL-FR1", "VL-FR2", "VL-FR3", and "VL-FR4".

The variable regions of a light chain and a heavy chain include three complementarity-determining regions (hereinafter, "CDR") and four framework regions (FR). The CDRs mainly serve to bind to the epitope of an antigen. The CDRs of each chain are typically called CDR1, CDR2, and CDR3 sequentially from the N-terminus, and are also distinguished by the chain where a specific CDR is located.

As used herein, the term "complementarity-determining region (CDR)" refers to a non-contiguous antigen binding site found within the variable regions of both heavy and light chain polypeptides. These specific regions are described in literature references (Kabat et al., *J. Biol. Chem.* 252, 6609-6616 (1977); Kabat et al., *Sequences of protein of immunological interest.* (1991); Chothia et al., *J. Mol. Biol.* 196:901-917 (1987); and MacCallum et al., *J. Mol. Biol.* 262:732-745 (1996)), which are incorporated herein by reference in their entirety. The definition above includes overlaps or subsets of amino acid residues when compared to one another.

The antibody or antigen-binding fragment of the present disclosure may have a heavy chain variable domain comprising HCDR1 represented by SEQ ID NO: 9; HCDR2 represented by SEQ ID NO: 10; and HCDR3 represented by SEQ ID NO: 3; and a light chain variable domain comprising LCDR1 represented by SEQ ID NO: 4; LCDR2 represented by SEQ ID NO: 5; and LCDR3 represented by SEQ ID NO: 6, in which the HCDR and LCDR may be defined by the Chothia numbering system.

The antibody or antigen-binding fragment of the present disclosure may have a heavy chain variable domain comprising HCDR1 represented by SEQ ID NO: 1; HCDR2 represented by SEQ ID NO: 2; and HCDR3 represented by SEQ ID NO: 3; and a light chain variable domain comprising LCDR1 represented by SEQ ID NO: 4; LCDR2 represented by SEQ ID NO: 5; and LCDR3 represented by SEQ ID NO: 6, in which the HCDR and LCDR may be defined by the Kabat numbering system.

In an embodiment of the present disclosure, the term "CDR" is a CDR defined by the Chothia numbering based on sequence comparison.

The antibody or antigen-binding fragment thereof of the present disclosure may have a heavy chain variable domain represented by SEQ ID NO: 7. The antibody or antigen-binding fragment thereof of the present disclosure may have a light chain variable domain represented by SEQ ID NO: 8. In an embodiment, the antibody or antigen-binding fragment thereof of the present disclosure may have a heavy chain variable domain represented by SEQ ID NO: 7 and a light chain variable domain represented by SEQ ID NO: 8.

The antibody of the present disclosure that binds to TM4SF5 protein is an antibody which can inhibit the activity of the TM4SF5 protein by binding to the TM4SF5 protein, and has the characteristic of binding to the TM4SF5 protein with high affinity.

As used herein, the term "transmembrane 4 L6 family member 5 (TM4SF5)", which is a type belonging to the transmembrane 4 superfamily (TM4SF) that is a group of membrane receptors that pass through the cell membrane 4 times, refers to a protein that mediates signaling pathways involved in cell development, activation, growth, differentiation, gene expression, and regulation of migration. The TM4SF5 protein has four domains that pass through the cell membrane, two loop structures present extracellularly, and one loop structure and two terminal structures present in the cytoplasm. Between the two loop structures present extracellularly, the length of EC2 (second external loop, extracellular loop 2) is longer than EC1 (first external loop, extracellular loop 1) and key amino acid residues involved in interactions with other molecules are present in EC2.

The type of the TM4SF5 protein is not particularly limited, but may preferably be a human TM4SF5 protein. Additionally, the TM4SF5 protein includes both native and mutant TM4SF5 proteins, but is not limited thereto. The native TM4SF5 protein generally refers to a polypeptide including the amino acid sequence of the native TM4SF5 protein, and the amino acid sequence of the native TM4SF5 protein generally refers to the amino acid sequence found in naturally occurring TM4SF5 protein. The information on TM4SF5 can be obtained from a known database (e.g., GenBank of the National Institutes of Health, etc.), and for example, it may be information on the TM4SF5 protein with an Accession Number of NP_003954 (Gene ID: 9032), but is not limited thereto.

The antibody of the present disclosure may be a humanized antibody.

As used herein, the term "humanized antibody" refers to an antibody prepared in such a form where part or the entirety of a CDR sequence of a mouse monoclonal antibody is grafted to a human antibody. For example, the humanized antibody may be obtained by preparing a humanized variable region by recombination between the CDRs of a mouse monoclonal antibody and human antibody-derived FRs, followed by recombination between the resultant and the constant region of a desirable human antibody.

Meanwhile, as used herein, the expression having an amino acid sequence represented by a specific SEQ ID NO can be understood as including the amino acid sequence, and in some embodiments, the expression may be modified to "consist essentially of" or "consist of" the amino acid sequence.

In an exemplary embodiment of the method for preparing the antibody of the present disclosure, the method may be performed by producing a hybridoma using B lymphocytes obtained from immunized animals (Koeher and Milstein, 1976, *Nature,* 256:495) or may be performed using phage display technology, etc., but is not limited thereto.

An antibody library using a phage display is a method of expressing an antibody on the surface of a phage with the gene of the antibody directly obtained from B lymphocytes without the preparation of hybridoma. Many of the existing difficulties associated with the monoclonal antibody production via B-cell immortalization can be overcome by using the phage display method. A conventional phage display method consists of: 1) inserting an oligonucleotide with a random sequence into the region corresponding to the N-terminus of a phage coat protein pIII (or pIV); 2) expressing a fusion protein between a part of a natural-type coat protein and a polypeptide encoded by the oligonucleotide having a random sequence; 3) treating a receptor material that can bind to the polypeptide encoded by the oligonucleotide; 4) eluting peptide-phage particles bound to the receptors at a low pH condition or using a binding-competitive molecule; 5) amplifying the eluted phage in a host cell by panning; 6) repeating the above steps to obtain a desired amount of phage; and 7) determining the sequence of a peptide with activity from the DNA sequences of the phage clones selected by panning.

In an embodiment, the method for preparing the monoclonal antibody of the present disclosure may be performed using a phage display technology. Those skilled in the art can easily perform the preparation of an antibody of the present disclosure with reference to known phage display technology, for example, the methods disclosed in literature references including Barbas et al. (*METHODS: A Companion to Methods in Enzymology* 2:119, 1991 and J. Virol. 2001 July; 75(14):6692-9) and Winter et al. (*Ann. Rev. Immunol.* 12:433, 1994). In an embodiment, known yeast display technology may also be used.

The polynucleotide encoding the monoclonal antibody or display clone of the present disclosure can easily be isolated and sequenced/analyzed using conventional procedures. For example, oligonucleotide primers designed to specifically amplify the heavy chain and light chain regions of interest from a hybridoma or phage template DNA may be used. Once the polynucleotide is isolated, it can be inserted into an expression vector, which is then transformed into a suitable host cell, and a desired monoclonal antibody can be obtained from the transformed host cell (i.e., transformants).

Accordingly, the method for preparing an antibody or antigen-binding fragment thereof of the present disclosure may include amplifying a polynucleotide encoding the antibody or antigen-binding fragment thereof in an expression vector including the polynucleotide encoding the antibody or antigen-binding fragment thereof, but is not limited thereto.

The expression vector including a polynucleotide encoding an antibody or antigen-binding fragment thereof of the present disclosure may include, although not particularly limited thereto, a vector capable of replicating and/or expressing the polynucleotide in eukaryotic or prokaryotic cells, including mammalian cells (e.g., human, monkey, rabbit, rat, hamster, mouse cells, etc.), plant cells, yeast cells, insect cells and bacterial cells (e.g., *E. coli*, etc.). The expression vector may be a vector which is operably linked to a suitable promoter so that the polynucleotide can be expressed in a host cell and includes at least one selective marker. For example, the expression vector may be in a form in which the polynucleotide is introduced into various viral vectors including a phage, plasmid, cosmid, mini-chromosome, retrovirus, etc.

The expression vector including the polynucleotide encoding an antibody or antigen-binding fragment thereof may be an expression vector including each of the polynucleotide encoding the heavy chain or light chain of the antibody, or an expression vector including both polynucleotides encoding the heavy chain and light chain of the antibody.

In the present disclosure, the transformants into which the expression vector is introduced may include, although not particularly limited thereto, bacterial cells (e.g., *E. coli, Streptomyces, Salmonella typhimurium* cells, etc.); yeast cells; fungal cells (e.g., *Pichia pastoris* cells, etc.); insect cells (e.g., *Drosophila, Spodoptera* Sf9 cells, etc.); animal cells (e.g., Chinese hamster ovary (CHO), SP2/0 (mouse myeloma), human lymphoblastoid, COS, mouse myeloma (NSO), 293T, Bowes melanoma, HT-1080, baby hamster kidney (BHK), human embryonic kidney (HEK), PERC.6 cells (human retinal cells), etc.); and plant cells which were transformed by the introduction of expression vectors.

As used herein, the term "introduction" refers to a method of delivering the vector including a polynucleotide encoding an antibody or antigen-binding fragment thereof into a host cell. Such introduction may be performed by various methods known in the art, including calcium phosphate-DNA co-precipitation, DEAE—dextran-mediated transfection, polybrene-mediated transfection, electroporation, microinjection, liposome fusion, various liposome including lipofectamine and protoplast fusion methods, etc. Additionally, transfection refers to a delivery of a target material into a cell by means of infection using viral particles. Further, the vector may be introduced into a host cell by gene bombardment. In the present disclosure, the term "introduction" may be used interchangeably with the term "transfection".

The pharmaceutical composition of the present disclosure may further include a pharmaceutically acceptable carrier in addition to the antibody or antigen-binding fragment thereof of the present disclosure, and the carrier may include a carrier which does not occur naturally.

As used herein, the term "pharmaceutically acceptable carrier" refers to a carrier or diluent that neither cause an irritation to an organism nor inhibit the biological activities and properties of the the compound to be administered. Examples of the pharmaceutically acceptable carriers to be used to formulate the composition in the form of liquid solutions, as sterile and biocompatible ones, may include saline solution, sterile water, Ringer's solution, buffered saline solution, albumin injection solution, dextrose solution, maltodextrin solution, glycerol, ethanol, and a mixture of one or more of these components thereof, and upon necessity, may also include other conventional additives (e.g., antioxidants, buffers, bacteriostatic agents, etc.). Additionally, the composition may further include diluents, dispersants, surfactants, binders, and lubricants to be formulated into injectable formulations (e.g., aqueous solutions, suspensions, emulsions, etc.), pills, capsules, granules, or tablets.

The pharmaceutical composition may have any one formulation selected from the group consisting of tablets, pills, powders, granules, capsules, suspensions, liquid solutions for internal use, emulsions, syrups, sterilized aqueous solutions, non-aqueous solvents, suspensions, emulsions, freeze-dried formulations, and suppositories, and may be in the form of various oral or parenteral formulations. The pharmaceutical composition is formulated using commonly used diluents or excipients, including fillers, extenders, binders, wetting agents, disintegrants, surfactants, etc. Solid formulations for oral administration include tablets, pills, powders, granules, capsules, etc. These solid formulations are prepared by mixing at least one compound with at least one excipient (e.g., starch, calcium carbonate, sucrose or lactose, gelatin, etc.). In addition to simple excipients, lubricants such as magnesium stearate and talc may also be used. Additionally, liquid formulations for oral administration may include suspensions, solutions for internal use, emulsions, syrups, etc. In addition to simple excipients, lubricants (e.g., magnesium stearate, talc, etc.) are also used. Liquid formulations for oral administration include suspensions, liquid solutions for internal use, emulsions, syrups, etc., and various excipients (e.g., wetting agents, sweetening agents, fragrances, preservatives, etc.) may be included in addition to the commonly used simple diluents (e.g., water and liquid paraffin). Formulations for parenteral administration include sterilized aqueous solutions, non-aqueous solvents, suspending agents, emulsions, lyophilized agents, and suppositories. As non-aqueous solvents and suspending agents, propylene glycol, polyethylene glycol, vegetable oils (e.g., olive oil), injectable esters (e.g., ethyl oleate), etc. may be used. As bases for suppositories, Witepsol, Macrogol, Tween 61, cacao butter, laurin butter, glycerinated gelatin, etc. may be used.

Additionally, the pharmaceutical composition of the present disclosure may be administered in a pharmaceutically effective amount.

As used herein, the term "pharmaceutically effective amount" refers to an amount sufficient to treat diseases, at a reasonable benefit/risk ratio applicable to medical treatment. The effective dose level of the composition may be determined depending on the subject's type, severity of disease, sex and age of the subject, type of disease, activities of the drug, sensitivity to the drug, duration of administration, administration route, excretion rate, length of treatment, drugs simultaneously used in combination with the composition, and other well-known factors in the medical field. The composition of the present disclosure may be administered as an individual therapeutic agent or in combination with other therapeutic agents, and sequentially or simultaneously with conventional therapeutic agents. The composition can be administered in a single or multiple dosage form. It is important to administer the composition in a minimum amount that can exhibit the maximum effect without causing side effects, in view of all the above-described factors, and the dose can easily be determined by those skilled in the art.

Additionally, the pharmaceutical composition may be administered orally or parenterally (e.g., intravenous, subcutaneous, intraperitoneal, or topical application) depending on the desired method. For example, the pharmaceutical composition may be administered parenterally.

The pharmaceutical composition of the present disclosure may be administered as an individual therapeutic agent or together with other active ingredients exhibiting preventive or therapeutic effects on TM4SF5-related diseases. When the pharmaceutical composition of the present disclosure is administered together with other active ingredients, this administration may be called "combination administration", "co-administration" or "complex administration", and in particular, the antibody or antigen-binding fragment thereof that specifically binds to TM4SF5 of the present disclosure and other active ingredients may be administered as a mixture or in a separate form.

In the present disclosure, the terms "co-administration", "co-administered", and "co-administering" should be understood as referring to simultaneous, individual, sequential, or reverse order administration, in any order. That is, the co-administration is not merely limited to simultaneous administration, but it may be a form of administration in which each material can exhibit a level equal to or higher than its original function by acting together on the subject. Therefore, when the term "co-administration" is used herein, if the administration is performed sequentially, in a reverse order, or individually, the order of administration is not particularly limited, and the interval of administration of the second component can be determined so as to ensure that the beneficial effects of the combination are not lost.

For example, the pharmaceutical composition of the present disclosure may be administered with a material selected from the group consisting of 5-fluorouracil (5-FU), oxaliplatin, doxorubicin, sorafenib, and cetuximab.

In an embodiment of the present disclosure, doxorubicin or sorafenib was administered in combination with the antibody of the present disclosure and thereby the excellent effect resulting therefrom was confirmed.

TM4SF5-related diseases of the present disclosure are diseases caused by overexpression of TM4SF5. For example, the TM4SF5-related diseases may be selected from the group consisting of fatty liver, steatohepatitis, liver fibrosis, liver cirrhosis, portal hypertension, liver cancer, stomach cancer, colorectal cancer, rectal cancer, oral cancer, pharynx cancer, larynx cancer, lung cancer, colon cancer, breast cancer, cervical cancer, endometrial cancer, ovarian cancer, prostate cancer, testicular cancer, bladder cancer, kidney cancer, pancreatic cancer, bone cancer, connective tissue cancer, skin cancer, brain cancer, thyroid cancer, leukemia, Hodgkin's disease, soft tissue sarcoma, lymphoma, multiple myeloma, and blood cancer.

For example, in cancer, TM4SF5 proteins induce epithelial-mesenchymal transition (EMT), which is involved in development, invasion, or metastasis of cancer, and ultimately causes the loss of contact inhibition of cells thereby leading to a multilayer growth (Lee S A et al., *J Clin Invest* 2008, 118(4):1354-66). Additionally, TM4SF5 proteins intracellularly interact with integrin α-5 to thereby activate the signaling process of FAK/c-Src/STAT3 and cause the expression and secretion of vascular endothelial growth factor (VEGF), an important factor in angiogenesis, thereby causing angiogenesis of vascular endothelial cells (Choi S et al., *Blood* 2009 113(8):1845-55). Accordingly, any material which can inhibit the function of TM4SF5 can exhibit an anticancer effect.

In an embodiment of the present disclosure, the effect of an antibody, which specifically binds to TM4SF5 protein, on the improvement of symptoms of colon cancer, liver cancer, prostate cancer, stomach cancer, etc. was confirmed; therefore, the antibody or antigen-binding fragment thereof of the present disclosure can be used for the prevention or treatment of diseases caused by overexpression of TM4SF5 protein.

As used herein, the term "prevention" may refer to all actions that can inhibit or delay the development of diseases by administering the composition of the present disclosure. Additionally, as used herein, the term "treatment" may refer to all actions that can restore or beneficially change the symptoms of cancer by administering the composition.

Overexpression of TM4SF5 protein is observed in various cells and is associated with the development of various diseases. Therefore, the antibody or antigen-binding fragment thereof of the present disclosure, which binds to TM4SF5 protein with high specificity and affinity, can be used for diagnosing diseases related to the presence/absence of TM4SF5 protein expression or an expression level thereof.

In the method for providing information for diagnosis, the TM4SF5 protein can be detected by reacting the TM4SF5-specific antibody of the present disclosure with a biological sample isolated from the subject suspected of having a disease, and detecting the formation of an antigen-antibody complex, whereby TM4SF5-related disease can be diagnosed, and through this method, information for disease diagnosis can be provided. The TM4SF5-related disease is as described above.

Specifically, the method may be a method for providing information for TM4SF5-related disease diagnosis or TM4SF5-related disease diagnosis method, which includes: (a) treating the antibody to an isolated biological sample of a subject suspected of having a TM4SF5-related disease and detecting TM4SF5 protein through an antigen-antibody reaction; and (b) comparing the level of TM4SF5 protein detected in (a) with that of the control group, and if the TM4SF5 protein level is higher than that of the control group, the subject is determined as a patient having the TM4SF5-related disease. The TM4SF5-related disease is as described above.

As used herein, the term "biological sample" may include a tissue, a cell, whole blood, serum, plasma, a tissue autopsy sample (e.g., brain, skin, lymph node, spinal cord, etc.), a cell culture supernatant, a ruptured eukaryotic cell, a bacterial expression system, etc., but is not limited thereto. The presence of the TM4SF5 protein or the presence/absence of cancer can be confirmed by reacting these biological samples with the antibody of the present disclosure in a manipulated or unmanipulated state.

As used herein, the term "antigen-antibody complex" refers to a conjugate between a TM4SF5 protein antigen in a sample and an antibody capable of recognizing the TM4SF5 protein antigen. The formation of such antigen-antibody complex can be detected by any method, such as a colorimetric method, an electrochemical method, a fluorimetric method, a luminometric method, a particle counting method, visual assessment, and a scintillation counting method, but the method is not limited thereto, and various methods may be used and applied.

Various labels may be used to detect the antigen-antibody complex. Specific examples of the label may include enzymes, fluorescent materials, ligands, luminescent materials, microparticles, and radioactive isotopes, but are not limited thereto. Examples of the enzymes that may be used as the detection label include acetylcholinesterase, alkaline phosphatase, β-D-galactosidase, horseradish peroxidase, β-latamase, etc. Examples of the fluorescent materials include fluorescein, $Eu^{3+}$, $Eu^{3+}$ chelate, cryptate, etc. Examples of the ligands include biotin derivatives, etc. Examples of the luminescent materials include acridinium ester, isoluminol derivatives, etc. Additionally, examples of the microparticles include colloidal gold, colored latex, etc. Examples of the radioactive isotopes include $^{57}Co$, $^{3}H$, $^{125}I$, $^{125}I$-Bonton Hunter reagents, etc.

In an embodiment, the antigen-antibody complex may be detected by an ELISA method. Examples of the ELISA method include a direct ELISA which uses a labeled antibody capable of recognizing an antigen attached to a solid support; an indirect ELISA which uses a labeled secondary antibody capable of recognizing a capture antibody in an antibody complex capable of recognizing an antigen attached to a solid support; a direct sandwich ELISA which uses another labeled antibody capable of recognizing an antigen in an antigen-antibody complex attached to a solid support; and an indirect sandwich ELISA, which includes reacting with another antibody capable of recognizing an antigen in an antigen-antibody complex attached to a solid support and then using the labeled secondary antibody capable of recognizing the antibody, etc.

The antibody may have a detection label. When the antibody has no detection label, the antibody can be captured and detection can be performed by treating with another antibody having a detection label.

Advantageous Effects

The antibody of the present disclosure can be effectively used for prevention, treatment, and diagnosis of diseases in which TM4SF5 protein is overexpressed.

BRIEF DESCRIPTION OF DRAWINGS

Values shown in graphs included in the drawings of the present disclosure represent means±standard deviation (SD).

FIGS. 1a, 1b, 2, 3 and 4 show the results confirming the anticancer activity of Ab27 against growth and metastasis of hepatocellular carcinoma (HCC) in a xenograft mouse model. *P<0.05; **P<0.01. P values are shown in the graphs.

FIG. 1a shows the results where SNU449T$_7$-luc (stably overexpressing TM4SF5 and luciferase) cells were orthotopically injected into mouse liver after minimal incision, and on day 7, Ab27 (100 μg/mouse) was intraperitoneally injected 2 to 3 times per week for 3 weeks (total of 8 injections). Left: Up to 27 days after cell injection, bioluminescence images were acquired. Right upper: Total bioluminescence flux for 3 weeks of treatment. Right lower: Body weight of injected mice.

In FIG. 1b, (A) shows bioluminescence images on day 14 and day 31 after cell injection, (B) shows the total bioluminescence flux for 2 weeks of treatment acquired using an IVIS Luminar imaging system, and (C) shows the body weight of injected mice. Values represent means±standard deviation (SD).

FIG. 2 shows the results of evaluating the anticancer activity of Ab27 in the sorafenib-resistant SNU449T7 cell xenograft model. Left upper: tumor volume (length×width$^2$/2) (the minimum value per group was excluded from the mean calculation). Middle: Body weight of injected mice. Bottom: a photograph of dissected tumor masses on day 30. Right: Immunoblot analysis of tumor extracts. α-Tubulin was used as internal control.

FIGS. 3 and 4 show the results of Intraperitoneal injection of Ab27 (300 μg/mouse), cetuximab (300 μg/mouse), or sorafenib (600 μg/mouse) into mice (total of 6 injections). In FIG. 3, the graph on the top represents tumor volume (length×width$^2$/2) and the graph on the bottom represents the body weight of injected mice. In FIG. 4, Ki67 staining was performed to measure the level of cell proliferation, and representative images are shown on the bottommost. Proliferative index (%) was measured as described in Materials and Methods. Scale bar (250 μm).

FIGS. 5 to 8 show the results confirming the anticancer activity of Ab27 against growth of colorectal cancer in a xenograft mouse model. *P<0.05; **P<0.01. P values are shown in the graphs.

FIG. 5 shows graphs for tumor volume (length×width$^2$/2) (the minimum value per group was excluded from the mean calculation) and the body weight of injected mice, and photographs for tumor-bearing mice on day 33.

In FIG. 6, the image on the left shows the measurement results of cell proliferation level through Ki67 staining of tumor parts. Proliferative index (%) was measured as described in Materials and Methods. Scale bar (100 μm).

The image on the right shows cell death area measured from the results from the left using ImageJ.

FIG. 7 shows the results where HT-29 cells were incubated with Ab27 (25 µg/mL) for 48 hours under suspension culture conditions, and then stained with annexin V and PI for flow cytometry.

FIG. 8 shows the results of immunoblot analysis of tumor extracts.

FIGS. 9 to 15 show the results confirming that Ab27 inhibits cancer cell growth by potential suppression of TM4SF5-mediated STAT3 phosphorylation. *P<0.05; **P<0.01. P values are shown in the graphs.

FIG. 9 shows the results of performing immunoblot analysis (top) and flow cytometry using Ab27 (bottom).

FIG. 10 shows the results where cells were transfected with TM4SF5-specific siRNA and immunostained using Ab27 (µg/mL) (green). Scale bar (50 µm).

FIG. 11 shows the results of internalization analysis.

FIG. 12 confirms the effect of STAT3 suppression on cell proliferation. CP<0.01; **P<0.001).

FIG. 13 shows the results where SNU449Tp cells were treated with DyLight 488 (green), conjugated with Ab27, at 37° C. for 3 hours, and stained with LysoTracker red DND-99 (red) and the immunoblot analysis results. Cell nuclei were counterstained with DAPI (blue). Arrows indicate signal co-localization. Scale bar (20 µm). Cells were transfected with TM4SF5-specific siRNA for 48 hours before lysis for immunoblot analysis.

FIG. 14 shows scatter plots representing TM4SF5 mRNA expression (x axis) and phosphorylated STAT3 at Tyr705 (y-axis) from liver hepatocellular carcinoma data.

FIGS. 15a and 15b show the results of immunoblot analysis after co-cultivation of Ab27, SNU-398, and HT-29 cells (FIG. 15a) and the results of anchorage-independent growth assay in the presence of Ab27 (FIG. 15b).

FIGS. 16 to 19 show the results of evaluation of cross-reactivity and in vivo toxicity of Ab27.

A and B of FIG. 16 each show the results of SDS-PAGE analysis of purified recombinant antigen proteins (human EC2-mouse Fc(hEC2-mFc)) and mouse EC2-mouse Fc(mEC2-mFc)) (A of FIG. 16) and purified Ab27 scFv-6× His-HA form (B of FIG. 16). (R: reducing; NR, non-reducing conditions). C of FIG. 16 shows the results of antigen binding ELISA.

FIG. 17 shows the results of immunoblot analysis using rabbit anti-TM4SF5 (in-house); the results of flow cytometry analysis with Ab27 (0.05 µg/sample); and the results of immunostaining of CT-26 cells (Ab27 (3 µg/mL): green). Scale bar (50 µm).

FIG. 18 shows the results of transfecting PC3 cells with mouse TM4SF5 expression vector followed by immunoblot analysis using anti-HA and anti-mouse TM4SF5 (in-house) antibodies; and the results of flow cytometry analysis using Ab27.

FIG. 19 shows the results of assessing the liver function of mice after intravenous injection of Ab27 (48 mg/kg) or control IgG by measuring serum concentrations of ALT, AST, ALP, GGT, Tbil, Dbil, ALB, and T-PRO. (Tbil: total bilirubin; T-pro: total protein; ALB: albumin; BW: body weight).

Figure 21:
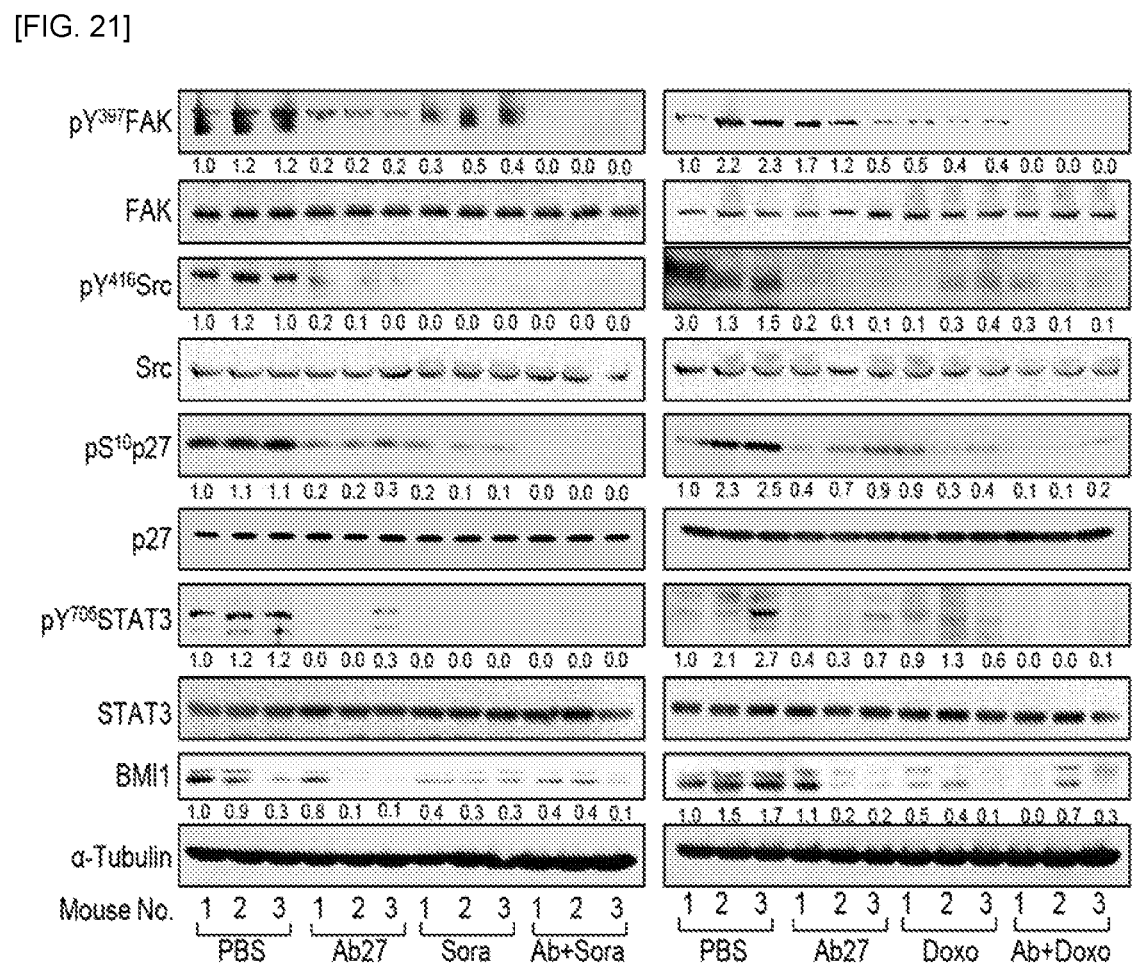

FIGS. 20 and 21 show the results confirming the anticancer efficacy of combined treatment of Ab27 and sorafenib or doxorubicin.

FIG. 20A shows tumor volume (length×width$^2$/2) when treated with a combination of Ab27 and sorafenib and a combination of Ab27 and doxorubicin. Values for both the IgG control and Ab27 treatment groups are presented repeatedly in both graphs. FIG. 20B shows a photograph of dissected tumor masses and FIG. 20C shows the body weight of injected mice. CP<0.05).

FIG. 21 shows the results of immunoblot analysis of tumor extracts. Densitometric quantification of bands on the immunoblot was performed using α-tubulin as a loading control, while excluding normalized phosphorylated proteins against the corresponding total protein.

FIGS. 22a and 22b show the results of in silico immunogenicity analysis. In the visualized results, colors indicate the degree of immunogenicity of an amino acid sequence determined by the percentile rank. Immunogenic sequences of on the heat map are each represented by 25%, 35%, and 50% cut-offs for low (P10, yellow), medium (P5, orange), and high (P1, red). (VH: heavy chain variable domain; VL: light chain variable domain). FIG. 22c represents the structure of Ab27-hz9.

FIG. 23 shows the results of SDS-PAGE analysis of purified Ab27-hz9 followed by Coomassie brilliant blue staining. Human IgG was loaded for comparison. (R: reducing; NR: non-reducing condition).

FIGS. 24 to 26 show the results of target recognition of humanized antibody Ab27-hz9.

FIGS. 24 and 25 show the flow cytometry of SNU449Cp and SNU449Tp cells using Ab27 and Ab27-hz9 (FIG. 24) and immunocytochemistry (FIG. 25). Scale bar (50 µm).

FIG. 26 shows the results of internalization analysis of SNU449Tp cells using Ab27 and Ab27-hz9.

FIG. 27 shows the results confirming the anticancer activity of humanized antibody Ab27-hz9 (*P<0.05; **P<0.01). In A of FIG. 27, the graph on the top represents tumor volume (length×width$^2$/2); the graph on the bottom represents the body weight of injected mice; and the photograph on the right shows tumor-bearing mice on day 33. B of FIG. 27 shows the results of Ki67 staining of tumor parts. Scale bar (250 µm). Values represent means±standard deviation (SD).

FIG. 28 shows the results confirming in vivo tumor targeting of Ab27 and Ab27-hz9 in a xenograft model. Whole body of mice, mice dissected at 96 hours (arrows indicate tumor mass), dissected tumor mass, total fluorescence flux of tumor mass were measured. (*P<0.01; **P<0.001).

FIG. 29 shows the results confirming in vivo tumor targeting of Ab27 and Ab27-hz9 in an endogenous TM4SF5-expressing liver cancer xenograft model. Whole body of mice, mice dissected at 96 hours (arrows indicate tumor mass), dissected tumor mass, total fluorescence flux of tumor mass were measured. (**P<0.01).

DETAILED DESCRIPTION OF THE INVENTION

Hereinafter, the present disclosure will be described in more detail with reference to the following Examples and Experimental Examples. However, these Examples and Experimental Examples are for illustrative purposes only and the scope of the present disclosure is not limited by these Examples and Experimental Examples.

Example 1. Materials and Methods

The experimental materials and experimental methods used in Example 2 are described in this Example.
scFv-hFc Production A monoclonal antibody Ab27 and its humanized monoclonal antibody Ab27-hz9 were produced using the Expi293™ or ExpiCHO™ Expression system (Thermo Fisher Scientific, 130 Waltham, Mass.) and purified using Protein A affinity chromatography with MabSelect™ SuRe™ Column (GE healthcare, Uppsala, Sweden) or as described in a literature (*Theranostics*, 2017. 7 (3): p. 594-613).

Cell Cultures

Human embryonic kidney 293E (HEK293E), HCT-116, HT-29 (colon cancer), HepG2 (liver cancer), PC3 (prostate cancer), and CT26 (mouse colon cancer) cell lines were purchased from the American Type Culture Collection (ATCC; Manassas, VA, USA). SNU-398 (liver cancer) and SNU-638 (gastric cancer) cell lines were purchased from the Korean Cell Line Bank (KCLB; Seoul, Korea). HEK293E and HepG2 cells were maintained in DMEM with 10% fetal bovine serum (FBS) at 37° C. in 5% $CO_2$. HCT-116, HT-29, PC3, SNU-398, SNU-638, and CT26 cells were maintained in RPMI1640 with 10% FBS at 37° C. in 5% $CO_2$. The stable SNU449Cp (TM4SF5-low), SNU449Tp and SNU449$T_7$ (both high-TM4SF5) liver cancer cell lines were maintained as described in a literature (*J Clin Invest*, 2008. 118 (4): pp. 1354-66). Luciferase-expressing SNU449$T_7$ cells (SNU449$T_7$-luc) are described in a literature ((SNU449$T_7$-luc) *Hepatology*, 2015. 61 (6): pp. 1978-97). C8161 cells (melanoma) were provided by Dr. C-R Jung (KRIBB, Korea) (*Nat Med*, 2006. 12 (7): pp. 809-16).

Transfection with Short Interference RNA (siRNA)

Cells were transfected with siRNA specific to TM4SF5 (5'-GGACCAACACCAACCATCTCAGCTT-3') and scrambled siRNA (5'-ACGCACCACGATCTATATCGC-CAAC-3') using lipofectamine 2000 for 48 hours before analysis. STAT3-specific siRNA (5'-CAGCCTCTCTGCAGAATTCAA-3') was also used.

Flow Cytometry

To analyze antibody binding to TM4SF5, flow cytometry was performed using SNU449Cp, SNU449Tp, HEK293E, and CT26 cells. HCT-116, SNU-398, HT-29, C8161, and SNU-638 cells that had been transiently transfected with either a TM4SF5-specific siRNA or a negative control siRNA were also analyzed. Cells ($2 \times 10^5$) were incubated with Ab27 or Ab27-hz9 at 0.03 μg to 0.3 μg at 4° C. for 45 minutes in 100 μL PBS containing 1% BSA. The cells were washed twice with 1% BSA/PBS, followed by a 30-minute incubation with fluorescein isothiocyanate (FITC)-conjugated anti-human IgG (Fc-specific; Pierce, Rockford, Ill., USA). Viable propidium iodide (PI)$^-$ cells were analyzed for antibody binding using FACSCalibur (BD Immunocytometry System, San Jose, Calif., USA). To generate hemagglutinin (HA)-tagged mouse TM4SF5-expression vector, mouse TM4SF5 cDNA (Accession No. NM_029360.3) was subcloned into pCMV-HA-N vector (Clonetech, Mountain View, Calif.). PC3 cells transiently transfected with HA-tagged mouse TM4SF5-expression vector were incubated with Ab27 and anti-HA, and then analyzed by flow cytometry.

Immunoblot Analysis

Whole-cell lysates were prepared using radioimmunoprecipitation assay (RIPA) buffer, immunoblotted as described in the literature (*Carcinogenesis*, 2015. 36 (3): pp. 327-37), and analyzed using the following primary antibodies: anti-FAK, anti-phospho-p27 (S10), anti-p27, anti-c-Src, anti-δ-actin, anti-α-tubulin, and anti-glyceraldehyde 3-phosphate dehydrogenase (GAPDH); Santa Cruz Biotechnology, Santa Cruz, Calif., USA); anti-phospho-c-Src (Y416), anti-phospho-ERK1/2, anti-ERK1/2, anti-phospho-STAT3 (Y705), and anti-STAT3) (Cell Signaling, Danvers, Mass., USA); anti-phospho-FAK (Y397) (Abcam, Cambridge, UK); anti-BMI1 (Millipore, Temecula, Calif.); anti-vimentin (Sigma, St. Louis, Mo.); anti-HA (Roche, Mannheim, Germany); and rabbit anti-human TM4SF5 (*J Clin Invest*, 2008. 118 (4): pp. 1354-66), and rabbit anti-mouse TM4SF5, which was produced using a peptide-corresponding mouse TM4SF5 (amino acid residues 117 to 138; CLIDNKWDYHFQETE-GAYLRND) (by ProSci Inc. (Poway, Calif.)).

Immunocytochemistry

SNU-449Cp, SNU-449Tp, and HepG2 and HT-29 cells that had been transiently transfected with TM4SF5-specific siRNA were plated on coverslips and incubated for 48 hours. The cells were then fixed for 20 minutes in methanol and permeabilized with acetone for 1 minute. After blocking in 1% normal horse serum, the cells were incubated with Ab27 or Ab27-hz9 (3 mg/mL or 5 mg/mL), followed by a corresponding secondary antibody conjugated to FITC. The cells were counterstained with 4,6-diamidino-2-phenylindole (DAPI; Sigma) to visualize nuclei. Immunofluorescent images were acquired under a confocal microscope (LSM 510 META, Carl Zeiss, Jena, Germany).

Internalization Analysis

Cell-surface binding and subsequent internalization of Ab27 and Ab27-hz9 were analyzed using flow cytometry. Briefly, cells were incubated with Ab27 or Ab27-hz9 at 4° C. for 45 minutes, washed to remove unbound antibodies, and then either warmed to 37° C. to allow internalization or maintained at 4° C. Cells were transferred to ice-cold buffer to stop the occurrence of internalization and stained with FITC-conjugated anti-human IgG. PI$^-$ cells were analyzed by flow cytometry. The relative levels of Ab27 or Ab27-hz9 bound to the cell surface were calculated as the shift in the fluorescence signal of the antibody occupancy relative to that detected at the beginning of the internalization period.

In order to detect lysosomal localization of Ab27, SNU-449Tp cells were seeded on coverslips in a 6-well plate and incubated at 37° C. for 48 hours. Cells were incubated with Ab27 conjugated to DyLight 755 at 37° C. for 3 hours and stained with 200 nM LysoTracker red DND-99 (Thermo Fisher Scientific). The cells were counterstained with DAPI before observation with a confocal microscope.

ELISAs (Antigen Binding and Competition ELISAs)

The recombinant human EC2-Fc fusion protein (EC2 (amino acid residues 113 to 157) fused to the Fc of human IgG1) was previously described, and recombinant human EC2-mouse Fc (derived from mouse IgG2a) fusion protein and mouse EC2 (amino acid residues 112 to 156) were produced in a similar way.

A DNA fragment encoding human EC2 followed by glutathione S-transferase (GST) was subcloned into the pET21 vector (Novagen, Darmstadt, Germany). The recombinant human EC2 domain fused with GST was expressed in *E. coli* BL21 (DE3) and affinity purified using a glutathione-Sepharose 4B column (GE Healthcare).

Ab27 scFv sequence was subcloned into the pComb3× digested with SfiI. Ab27 scFv tagged with 6×His and HA was expressed in *E. coli* BL21 by IPTG induction (final concentration of 0.1 mM), and a periplasmic extract was obtained using the osmotic shock method (see *Mol Cells*, 2009. 27 (2): pp. 225-35). Ab27 of the ScFv-6×His-HA format was purified from the periplasmic extract by NI-NTA affinity chromatography.

For antigen binding ELISA, 96-well immunoplates (eBiosciences, San Diego, CA, USA) were coated with the purified hEC2-GST protein (100 ng/well) diluted in 50 mM sodium carbonated buffer (pH 9.6) at 4° C. overnight and then blocked with 2% BSA in PBS. The plates were washed 3 times with PBS containing 0.05% Tween 20 between all of the steps. Ab27 or Ab27-hz9 (amounts ranging from 0 ng/well to 90 ng/well) was added into each well, and then horseradish peroxidase (HRP)-conjugated anti-human Fc was added. All of the incubations were carried out at 37° C. for 1 to 2 hours. Color was developed with 3,3',5,5'-tetramethylbenizidine (TMB) substrate solution, and the absorbance was measured at 450 nm using a microplate reader (BMG LABTECH GmbH, Ortenber, Germany). Binding of Ab27 scFv-6×His-HA to hEC2-mFc or mEC2-mFc protein was analyzed using HRP-conjugated anti-HA in a similar manner.

For competition ELISA to determine affinity ($K_D$ value), 96-well plates were coated with the hEC2-GST protein. Ab27 or Ab27-hz9 (amount reaching absorbance 1, which was determined from the above antigen binding ELISA) were incubated with hEC2-GST protein ranging from 0 μM to 1 μM for 2 hours, and then the mixtures were put onto the plates for 1 hour. HRP-conjugated anti-human Fc incubation, color development, and absorbance measurement were performed as described above.

Construction of Humanized Antibody Ab27-Hz9

Six CDRs determined by combined Kabat/IMGT/Paratome numbering (*MAbs*, 2017. 9 (3): pp. 419-429) were grafted into the human IFHV1-2 and IGKV3-20 frameworks. Humanized heavy chain variable domain (VH) and kappa chain variable domain ($V_K$)-encoding genes were synthesized as an scFv format and then inserted into the pDR-OriP-Fc1 mammalian expression vectors (see *Theranostics*, 2017. 7 (3): pp. 594-613).

Surface Plasmon Resonance (SPR) Analysis

The kinetic parameters of the interaction between the scFv-Fc forms of Ab27 and Ab27-hz9 and hEC2-GST were determined at 25° C. using the Biacore T200 (Cytiva, Marlborough, Mass.). Briefly, anti-human Fc antibody was amine-coupled on a CM5 sensor chip using the Human Antibody Capture Kit (Cytiva) and then scFv-Fc was injected for 30 seconds at a flow rate of 10 μL/min according to the manufacturer's instructions. hEC2 GST in HBS-EP buffer with 350 mM NaCl at a concentration range of 12.5 nM to 100 nM was then injected for 3 minutes at a flow rate of 30 μL/min. After each binding cycle, a regeneration solution (3 M $MgCl_2$) was injected for 1 minute to remove any non-covalently bound protein. The association rate ($k_a$), dissociation rate ($k_d$), and equilibrium dissociation constant ($K_D$, $k_d/k_a$) were determined using a 1:1 binding model and Biacore BIAevaluation software version 1.0.

Cell Proliferation Assay

Cell proliferation was determined using the colorimetric WST-1 Cell Proliferation Assay Kit (Takara Bio Inc., Otsu, Shiga, Japan). Briefly, cells were seeded into 96-well plates at a density of $5×10^3$ cells/well and incubated for 48 to 72 hours in the presence of antibodies. The cells were then incubated with the WST-1 reagent ($1/10^{th}$ of the medium volume), and formazan dye formation was determined by measuring absorbance at 450 nm using a microplate reader.

Soft Agar Anchorage-Independent Growth Assay

Cells were seeded at a density of $1×10^3$ cells/well in 6-well tissue culture plates in 0.4% agar (Sigma) over a 0.6% agar feed layer. Cells were allowed to grow at 37° C. in 5% $CO_2$ concentration for 13 days, and the number of resulting colonies with diameter >0.3 mm or 0.5 mm was counted per well.

Anoikis Assay

Cells ($5×10^5$) were seeded in the presence of antibodies into 6-well plates with an Ultra-Low Attachment Surface (Corning) to induce anoikis. Cells were washed and stained with 5 μL of annexin V and 5 μL of PI per $1×10^5$ cells for 15 minutes at room temperature in the dark, and the percentage of apoptotic cells was analyzed using flow cytometry. The cells were harvested after the induction of anoikis, washed with PBS, and lysed for subsequent immunoblot analysis.

Mouse Xenograft Models

All of the animal procedures were performed in accordance with the procedures of the Seoul National University Laboratory Animal Maintenance Manual and Institutional Review Board (IRB) agreement (SNU-190122-6-3 and SNU-161222-3), and the guidelines of the Animal Care Committee at the Korea Research Institute of Bioscience and Biotechnology (KRIBB) and approval of the bioethics committed of KRIBB (KRIBB-AEC-17041, KRIBB-AEC-18094, KRIBB-AEC-19098, and KRIBB-AEC-20117). Nude mice (BALB/c-nude, 5 weeks old) were obtained from Japan SLC, Inc. (Japan) or Nara Biotech (Seoul, Korea). SNU449T$_7$-luc (stably overexpressing TM4SF5 and luciferase) cells were orthotopically injected into the liver ($5×10^5$ cells) after minimal incision or subcutaneously into the back ($1×10^6$ cells) (see *Hepatology*, 2015. 61 (6): pp. 1978-97). On day 7 and day 14, the mice were randomized into control and treatment groups. Ab27 (100 μg/mouse) was intraperitoneally (i.p.) injected at 2- or 3-day intervals for 2 or 3 weeks (7 or 8 times in total). Bioluminsecence from SNU449T$_7$ cells were acquired in an IVIS Luminar imaging system (Perkin Elmer, Santa Clara, CA) as described in (*Hepatology*, 2015. 61 (6): pp. 1978-97).

SNU449T$_7$ cells were treated with sorafenib (1 μM to 10 μM) for 2 weeks, and the surviving cells (sorafenib-resistant SNU449T$_7$; $1×10^6$ cells) were mixed with Matrigel on ice and then injected subcutaneously into the backs of the mice. After 11 days, when tumor volumes reached about 100 mm$^3$, the tumor-bearing mice were randomized into control and treatment groups (n=7 per group). Ab27 (250 μg/mouse) or sorafenib (400 μg/mouse) was intraperitoneally (i.p.) injected at 2- or 3-day intervals for 2 or 3 weeks (8 times in total).

SNU-398 ($1×10^7$) and HT-29 ($2.5×10^6$) cells were subcutaneously injected into the flank of each mouse. When volumes reached about 70 mm$^3$, the tumor-bearing mice were randomized into control and treatment groups (n=6 per group). Ab27 (300 μg/mouse), cetuximab (300 μg/mouse), or sorafenib (600 μg/mouse) was intraperitoneally (i.p.) injected at 2-day interval or twice per week (6 times in total). Normal human IgG (Sigma; 300 μg/mouse) or PBS was injected as a negative control.

For combination treatment, SNU449T$_7$ ($1×10^6$) cells were subcutaneously injected into the mice. When volumes reached about 100 mm$^3$, the tumor-bearing mice were randomized into control and treatment groups (n=6 per group). Ab27 (270 μg/mouse), sorafenib (1,200 μg/mouse), or doxorubicin (20 μg/mouse) was intraperitoneally (i.p.) injected twice per week (6 times in total). For the combination treatment group, Ab27 and sorafenib or doxorubicin were intraperitoneally (i.p.) injected at 6-hour intervals. Sorafenib was dissolved in DMSO/Cremophor EL/PBS (1:1:8).

SNU449T$_7$ ($1×10^7$) cells were subcutaneously injected into the flanks of mice. When volumes reached about 100 mm$^3$, the tumor-bearing mice were randomized into control and treatment groups (n=6 per group). Ab27, Ab27-hz9, or cetuximab (300 μg/mouse) was intraperitoneally (i.p.) injected at 2- or 3-day intervals (12 times in total). Normal human IgG was injected as a negative control.

Body weight and tumor volume were measured before injection of the antibody or drug. Tumor volumes were calculated using the formula width$^2$×length/2). Tumor masses were lysed as described in the literature for immunoblot analysis (*J Clin Invest*, 2008. 118 (4): pp. 1354-66) or tumor masses were fixed in 10% formalin and embedded in paraffin.

Immunohistochemistry

Formalin-fixed and paraffin-embedded 6-μm-thick tissue sections from xenograft tumors were processed for immunohistochemistry analysis as per the standard protocol. Sections were stained with anti-Ki67 antibody (SP6; Abcam) using the peroxidase technique. The proliferative index (%) was determined by calculating the number of Ki67$^+$ cells relative to the total number of cells, which consisted of at least 1,000 cells per field. Five randomly selected fields from tumor sections per mouse were analyzed using ImageJ software.

In Vivo Toxicity of Ab27

In vivo toxicity testing of Ab27 was performed by KBIOhealth (Osong, Korea). Six-week-old ICR mice (female, n=5) were intraperitoneally (i.p.) injected with 48 mg/kg of Ab27. General clinical signs including body weight were monitored. Twenty-eight days after injection, the mice were sacrificed, and urine and blood samples were collected. Standard hematological analysis and urinalysis were performed. Bloods samples were centrifuged at 1,700×g for 10 minutes, and biochemical parameters of serum were analyzed using a Konelab 60i (Thermo Scientific, Vantaa, Finland).

In Vivo Tumor Targeting

Ab27, Ab27-hz9, and normal human IgG were conjugated with DyLight 755 and purified using a DyLight 755 Antibody Labeling Kit (Thermo Scientific) according to the manufacturer's instructions. When the size of the tumor formed by SNU449T$_7$ or SNU-398 cell reached about 100 mm$^3$, 70 μg of dye-labeled antibody was injected into the tail vein of nude mice. The distribution profiles of the antibody were quantified by in vivo fluorescence using IVIS imaging system at 0, 24, 48, 72, and 96 hours after antibody injection. The tumor was removed at 96 hours after injection to determine the distribution of the DyLight755-labeled antibody in tumor tissues.

Analysis of the Cancer Genome Atlas (TCGA) Data cBioPortal (www.cbioportal.org) (see *Sci Signal*, 2013. 6 (269): p. pll; *Cancer Discov*, 2012. 2 (5): pp. 401-4) was used to analyze TCGA-generated human liver HCC data (TCGA, PanCancer Atlas). All of the patient samples with available mRNA and protein expression profiles were included in the correlation analysis.

Statistical Analysis

Statistical analysis was performed using the Student's t-test, one-way ANOVA (use of GraphPad Prism 8 (GraphPad Software, CA)), and Pearson's test. P<0.05 was considered statistically significant.

Example 2. Results of Experiments

Example 2-1. Anticancer Activity of Ab27 Against Growth and Metastasis of Hepatocellular Carcinoma (HCC) in a Xenograft Mouse Model The anticancer activity of systemically injected Ab27 was examined in a xenograft nude mouse model.

Example 2-1-1. Confirmation of Antitumor Effect of Ab27 on TM4SF5-Overexpressing SNU449T$_7$ TM4SF5-overexpressing SNU449T$_7$ cells (5×10$^5$) ectopically expressing the luciferase gene were orthotopically injected into the liver after minimal incision. On day 7, Ab27 (100 μg/mouse/dose) was intraperitoneally (i.p.) injected 3 times per week for a total of 8 times. PBS was injected as a negative control. In vivo imaging analysis revealed that Ab27 inhibited tumor growth by 64% without affecting body weight (FIG. 1*a*).

Similarly, the same tumor cells SNU449T$_7$-luc (1×10$^6$) were subcutaneously injected into the flanks of mice, and on day 14, Ab27 (100 μg/mouse) was intraperitoneally (i.p.) injected at 2- or 3-day intervals for 2 weeks (7 times in total). The results are shown in FIG. 1*b*. The administration of Ab27 (100 μg/mouse) suppressed tumor growth by about 66% (FIG. 1*b*).

Example 2-1-2. Evaluation of Anticancer Activity of Ab27 in Sorafenib-Resistant SNU449T$_7$ Cell Xenograft Model The antitumor activity of Ab27 was evaluated in a sorafenib-resistant SNU449T$_7$ cell xenograft model. TM4SF5-overexpressing SNU449T$_7$ cells were treated with sorafenib (1 μM to 10 μM; 3 culture medium changes per week) for 3 weeks, and the surviving sorafenib-resistant cells (1×10$^6$) were mixed with Matrigel and then subcutaneously injected into the flanks of the nude mice. Ab27 (250 μg/mouse) or sorafenib (400 μg/mouse) was injected at 2- or 3-day intervals (8 times in total).

As shown in FIG. 2, the administration of Ab27 (250 μg/mouse/dose) by intraperitoneal injection (3 times per week for a total of 8 times) significantly inhibited tumor growth by about 50%, based on mean tumor volume, whereas sorafenib (400 μg/mouse/dose) did not remarkably decrease tumor growth. Immunoblot analysis of xenograft tumor tissues showed that Ab27 decreased the phosphorylation of FAK (moderately), c-Src (moderately), p27$^{KiP1}$, and STAT3, and the expression of BMI1, whereas sorafenib relatively moderately decreased the phosphorylation of FAK, c-Src, p27$^{KiP1}$, and STAT3 (right of FIG. 2). Meanwhile, consistent with the results of previous studies, the expression of p27$^{KiP1}$ was not substantially changed by Ab27 in xenograft models established using SNU449T$_7$ cells. This may be due to the phosphorylation of p27$^{Kip1}$ at sites other than Ser10.

Example 2-1-3. Evaluation of Anticancer Activity of Ab27 in TM4SF5-Expressing SNU-398 Liver Cancer Xenograft Model The antitumor activity of Ab27 was evaluated in nude mice bearing liver cancer xenografts of SNU-398 cells expressing endogenous TM4SF5. SNU-398 cells were subcutaneously injected into the flanks of the mice. Ab27 (300 μg/mouse/dose), cetuximab (300 μg/mouse/dose), or sorafenib (600 μg/mouse/dose) was injected at 2- or 3-day intervals (6 times in total). Normal human IgG (300 μg/mouse) was injected as a negative control.

As shown in FIGS. 3 and 4, Ab27 significantly inhibited tumor growth by about 46% without affecting body weight. The antitumor activity of Ab27 was comparable with that of cetuximab and sorafenib, which inhibited tumor growth by 50% and 51%, respectively. Immunostaining of tumor sections showed that the injection of Ab27, cetuximab, or sorafenib significantly decreased the Ki67 proliferation index.

Example 2-2. Confirmation of Antitumor Activity of Ab27 Against Colon Cancer Growth in a Xenograft Model in Mice It is known that high levels of TM4SF5 correlated with worse overall survival of colorectal cancer (CRC) patients suggesting a potential role of TM4SF5 in colon cancer progression. Therefore, the antitumor efficacy of Ab27 in nude mice bearing colon cancer xenografts of HT-29 cells expressing endogenous TM4SF5 was examined.

HT-29 cells (2.5×10$^6$) were subcutaneously injected into the flanks of the mice and Ab27 (142 µg/mouse/dose) was intraperitoneally (i.p.) injected twice per week (6 times in total) into xenografted mice.

Ab27 administration inhibited tumor growth by about 38% without affecting body weight (FIG. 5). It was confirmed through immunostaining of tumor sections that the number of proliferative Ki-67 cells was significantly lower in tumors from mice injected with Ab27 than in tumors from control mice (left of FIG. 6). Additionally, the Ab27-treated tumors exhibited a larger area of cell death within the tumor core than control tumors (right of FIG. 6). These results suggest that Ab27 can accelerate necrosis or apoptosis induced by hypoxia (see *Cancer Res,* 1996. 56 (9): pp. 2161-6).

HT-29 cells were incubated with Ab27 (25 µg/mL) for 48 hours under suspension culture conditions, and then stained with annexin V and PI for flow cytometry. HA6 was used as a negative control antibody. The experimental results are shown in FIG. 7. Consistent with the results described above, Ab27 promoted apoptosis in HT-29 cells grown under suspension culture condition in vitro (FIG. 7). These results suggest that Ab27 inhibits tumor growth in vivo by inhibiting tumor cell proliferation and promoting tumor cell death.

The immunoblot analysis results for tumor tissue are shown in FIG. 8. Densitometric quantification of bands on the immunoblot was performed using GAPDH as a loading control except that phosphorylated STAT3 and ERK1/2 were normalized against the corresponding total protein. The experimental results showed that Ab27 decreased the phosphorylation of p27$^{Kip1}$ and STAT3 and the expression of p27$^{Kip1}$ and BMI1, but has a less substantial effect on the phosphorylation of ERK1/2 (FIG. 8). These results suggest that Ab27 can inhibit tumor growth in nude mice bearing TM4SF5$^+$ liver and colon cancer xenografts and that this can occur concomitantly with a reduction in the phosphorylation levels of STAT3 and p27$^{Kip1}$.

Example 2-3. Inhibition of TM4SF5-Mediated STAT3 Activation and Cancer Cell Growth by Ab27

In order to examine whether Ab27 specifically recognizes endogenous TM4SF5, flow cytometry was performed for cancer cells transiently transfected with TM4SF5-specific siRNA or negative control siRNA. Cells were transfected with TM4SF5-specific siRNA for 48 hours using rabbit anti-TM4SF5 (in-house), and then lysed to perform immunoblot assay. The results of flow cytometry performed using Ab27 are shown in FIG. 9. As shown in FIG. 9, Ab27 were bound to HCT-116, HT-29 (colon), SNU-398 (liver), SNU-638 (stomach), and C8161 (melanoma) cancer cells expressing endogenous TM4SF5, and the suppression of TM4SF5 expression by siRNA decreased the degree of Ab27 binding to these cells thus suggesting the specificity of Ab27.

Cells were transfected with TM4SF5-specific siRNA for 48 hours, immunostained using Ab27 (µg/mL) (green), and cell nuclei were counterstained with DAPI (blue). The results are shown in FIG. 10. As in the results of immunofluorescence staining, cell membranes and cytoplasm of HepG2 and HT-29 cells were substantially stained, whereas membranes of TM4SF5-inhibited cells were not stained (FIG. 10).

Then, in order to allow internalization of HCT-116 cells, the cells were incubated with Ab27. The HCT-116 cells were incubated with Ab27 (0.3 µg/sample) at 4° C. for 45 minutes, washed to remove unbound antibodies, and then either warmed to 37° C. to allow internalization or maintained at 4° C. for the indicated periods. FITC-conjugated anti-human IgG was analyzed by flow cytometry (FIG. 11). As a result of the experiment, the residual level of cell surface-bound Ab27 was significantly reduced (FIG. 11) suggesting that Ab27 was internalized after binding to endogenous TM4SF5 on the cell surface, thereby decreasing the cell-surface level of TM4SF5. This is consistent with the results reported in the literature where ectopically TM4SF5-overexpressing SNU449Tp cells were observed (*Theranostics,* 2017. 7 (3): pp. 594-613). Additionally, treatment of SNU-449Tp cells with DyLight 488-conjugated Ab27 for 3 hours followed by staining with LysoTracker to label lysosomes revealed that Ab27 was localized to lysosomes thus suggesting the rapid internalization and lysosomal targeting of Ab27.

Previously, it was reported that TM4SF5 activates STAT3 in HCC cells (see *Hepatology,* 2015. 61 (6): pp. 1978-97). STAT3 is known to facilitate cancer cell proliferation and survival, tumor spheroid formation, and metastasis (*Biochim Biophys Acta,* 2013. 1835 (1): pp. 46-60). SNU-638, SNU-398, and HT-29 cells were transfected for 48 hours using STAT3-specific siRNA, lysed to confirm whether STAT3 was inhibited, and used for the experiment of cell proliferation. Knockdown of STAT3 in SNU-638, SNU-398, and HT-29 cells decreased cell proliferation (FIG. 12) confirming the role of STAT3 in cell proliferation. Additionally, when the cells were transfected for 48 hours with TM4SF5-specific siRNA, and lysed to perform immunoblot assay, the SNU-398, HT-29, HepG2, and C8161 cells showed a decrease in phosphorylation of STAT3 and subsequent expression of BMI1 after inhibition of TM4SF5 (FIG. 13), thus being consistent with the study results reported in the literature (*Hepatology,* 2015. 61 (6): pp. 1978-97).

Additionally, analysis of TCGA-induced human liver hepatocellular carcinoma (TCGA, PanCancer Atlas) was performed. The correlation between the TM4SF5 mRNA expression and the phosphorylation of STAT3 at Tyr705 was statistically analyzed using the Pearson test, and the results are shown in FIG. 14. The equation was automatically generated using the cBioPortal webpage tool. From this, it was confirmed that the TM4SF5 mRNA expression is correlated with the phosphorylation of STAT3 at Tyr705 (FIG. 14).

Cells were incubated with Ab27 (250 µg/mL) under suspension conditions for 48 hours and analyzed. As a result, it was found that Ab27 decreased the phosphorylation of STAT3 and expression of BMI1 in SNU-398 and HT-29 cells, and significantly decreased the anchorage independent growth of SNU-398 and HT-29 cells in a dose-dependent manner. In the evaluation of anchorage independent growth, colonies (>0.5 mm for SNU-398 cells, >0.3 mm for HT-29 cells) were counted in six 100× fields per well. In line with the previous study results, the phosphorylation of FAK and p27$^{Kip1}$ and the expression were also decreased by TM4SF5 knockdown and Ab27. Additionally, Ab27 decreased the expression of vimentin in SNU-398 and HT-29 cells (FIG. 15).

These results indicate that Ab27 contributes to the reduction of cancer cell growth and suppresses TM4SF5-induced EMT events.

Example 2-5. Evaluation of Ab27 Cross-Reactivity and In Vivo Toxicity

The cross-reactivity of Ab27 with mouse TM4SF5 was examined. ELISA showed that Ab27 did not bind to recombinant mouse TM4SF5 EC2 protein as efficiently as it did to human TM4SF5 EC2 protein (FIG. 16).

Specifically, purified recombinant antigen proteins (human EC2-mouse Fc (hEC2-mFc) and mouse EC2-mouse Fc (mEC2-mFc)) and purified Ab27 scFv-6×His-HA form were analyzed by SDS-PAGE followed by Coomassie brilliant blue staining (A and B of FIG. 16). The results of antigen binding ELISA are shown in C of FIG. 16.

Specifically, 96-well immunoplates were coated with purified with hEC2-mFc or mEC2-mFc (100 ng/well) and then blocked with 2% BSA. Ab27 (scFv-6×His-HA form; serial diluted) was added, followed by HRP-conjugated anti-HA. A color was developed with a TMB substrate solution and the absorbance at 450 nm was measured at 450 nm.

Results of immunoblot analysis using rabbit anti-TM4SF5 (in-house); results of flow cytometry using Ab27 (0.05 µg/sample), and results of immunostaining of CT-26 cells (Ab27 (3 µg/mL) green; cell nuclei counterstained with DAPI (blue)) are shown in FIG. 17. Contrary to the ELISA results, the results of flow cytometry and immunofluorescence analyses showed that Ab27 recognized TM4SF4 in CT26 mouse colon cancer cells (FIG. 17).

PC3 human prostate cancer cells, which normally exhibit low endogenous TM4SF5 expression, were transiently (48 hours) transfected with HA-tagged mouse TM4SF5-expression vector. The results of flow cytometry revealed that Ab27 bound to PC3 cells more efficiently transfected with mouse TM4SF5-expression vector than to PC3 cells transfected with empty vector (FIG. 18), confirming reactivity with mouse TM4SF5. Therefore, the mouse is an appropriate species for studying safety in vivo.

In order to evaluate the in vivo toxicity of anti-TM4SF5 antibody, a single dose of Ab27 (48 mg/kg) or control IgG was intravenously (i.v.) injected to female ICR mice (n=5), and the blood sample was analyzed 28 after the antibody injection. Although TM4SF5 mRNA was expressed in the liver, TM4SF5 protein was not detected (https://genecards.org). Liver function was determined by measuring serum concentrations of general parameters, including alanine aminotransferase (ALT), aspartate aminotransferase (AST), alkaline phosphatase (ALP), γ-glutamyl transpeptidase (GGT), bilirubin, and albumin (FIG. 19).

As a result of the experiment, it was found that there were no general toxicities, including significant changes in liver function or body weight, thus indicating that Ab27 is not significantly toxic in vivo.

Example 2-6. Anticancer Efficacy in Combination Treatment of Ab27 and Sorafenib or Doxorubicin Sorafenib is a standard regiment for advanced HCC, and doxorubicin is an anticancer agent used for transcatheter arterial chemoembolization (TACE). For combined treatment with Ab27 and sorafenib or doxorubicin, preliminary experiments were performed to evaluate the antitumor efficacies of sorafenib and doxorubicin in the SNU449T$_7$ xenograft mouse model.

In the next experiment, submaximal schedules or doses of Ab27, sorafenib, and doxorubicin were injected into the SNU449T$_7$ xenograft mouse model to examine whether the combined treatment of Ab27 and the drugs could exhibit inhibition of tumor growth to a greater extent than Ab27 or the drugs alone.

SNU449T$_7$ ($1\times10^6$) cells were mixed with Matrigel and subcutaneously injected into the back, and then Ab27 (270 µg/mouse/dose); sorafenib (1,200 µg/mouse/dose); doxorubicin (20 µg/mouse/dose); a combination of Ab27 (270 µg/mouse/dose) and sorafenib (1,200 µg/mouse/dose) or a combination of doxorubicin (20 µg/mouse/dose); or saline (control) were intraperitoneally injected twice per week (6 times in total) into nude mice (n=6 per group) bearing SNU449T$_7$ xenografts.

As shown in A of FIG. 20, single treatment of Ab27, sorafenib, and doxorubicin inhibited tumor growth relative to the control by 25%, 42%, and 26%, respectively, whereas the combined treatment of Ab27 and sorafenib inhibited tumor growth by 54%, and the combined treatment of Ab27 and doxorubicin inhibited tumor growth by 52%. Therefore, it was found that the combined treatments inhibited tumor growth to a significantly greater extent than single treatments. Neither combined nor single-agent treatment affected body weight (B of FIG. 20). Immunoblot analysis of tumor lysates revealed that, relative to single treatment, the combined treatment of Ab27 and sorafenib enhanced the phosphorylation of FAK and p27$^{Kip1}$, and that the combined treatment of Ab27 and doxorubicin enhanced the phosphorylation of FAK, p27$^{Kip1}$, and STAT3 (FIG. 21) (In particular, it was not possible in this study to determine the effect of combination treatment because sorafenib abolished the phosphorylation of STAT3). Although the reduction of BMI1 by Ab27 was confirmed, additional reduction was not observed after combined treatment.

These results indicate that combined treatment of Ab27 and sorafenib or doxorubicin inhibits tumor growth more strongly than treatment with antibody or drug alone.

Example 2-7. Generation and Characterization of Humanized Monoclonal Antibody Ab27-hz9

For clinical applications of monoclonal antibodies, murine-related sequences of antibodies must be humanized so as to decrease immunogenicity in humans. Meanwhile, human germline genes have fewer intraclonal somatic hypermutations which can be recognized as immunogenic. Therefore, a humanized Ab27 was constructed by grafting murine complementarity-determining regions (CDRs) into similar human germline sequences (FIG. 22c).

The human germline V genes IGHV1-2 and IGKV3-20 were selected as human acceptor frameworks for the grafting of murine CDRs. However, such CDR grafting often results in partial or complete loss of affinity of the humanized antibody. Therefore, some residues from the murine framework sequences need to be retained by replacing human residues at the corresponding positions to restore some of the lost affinity. In this regard, murine framework sequences H71 and H73 were engrafted into the human framework. The final humanized antibody was named Ab27-hz9. Identification of immunogenic sequences was performed using the IEDB MHC II prediction server (*Nucleic Acids Res*, 2012, 40 (Web Server issue): pp. W525-30), which employs a consensus approach combining NN-align, SMM-align, CombLib, and Sturniolo methods. The results from the IEDB prediction were visualized using the web-based analysis system in KBIO Health (Osong, Korea) and are shown in FIGS. 22a, 22b and 22c.

In silico immunogenicity analysis predicted that the immunogenicity of Ab27-hz9 VH would be lower than those of adalimumab and omalizumab, which are currently used in the clinic, while the immunogenicity of the Ab27-hz9 light chain variable domain was predicted to be comparable to those of adalimumab and omalizumab (FIGS. 22a, 22b and 22c).

Humanized antibody Ab27-hz9 was produced in Expi293 cells (FIG. 23). The VH sequence of Ab27-hz9 is shown in SEQ ID NO: 7 and the VL sequence of Ab27-hz9 is shown in SEQ ID NO: 8. The HCDR1 sequence of Ab27 is represented by SEQ ID NO: 1 according to the Kabat numbering and by SEQ ID NO: 9 according to the Chothia numbering; the HCDR2 sequence is represented by SEQ ID NO: 2 according to the Kabat numbering and by SEQ ID NO: 10 according to the Chothia numbering; the HCDR3 sequence is represented by SEQ ID NO: 3; the LCDR1 sequence is represented by SEQ ID NO: 4; the LCDR2 sequence by SEQ ID NO: 5; and the LCDR3 sequence by SEQ ID NO: 6.

The reactivity of the generated humanized antibody Ab27-hz9 was evaluated.

As a result of flow cytometry using SNU449Cp and SNU44Tp cells, it was found that Ab27-hz9 as well as Ab27 was bound more efficiently to SNU449Tp cells than to SNU449Cp cells (FIG. 24). Additionally, immunofluorescence staining showed that Ab27-hz9 (with a stronger level) and Ab27 stained the membrane edges of SNU449Tp cells, but not those of SNU449Cp cells (FIG. 25). These results indicate that Ab27-hz9 recognizes TM4SF5 on the cell surface at least as strongly as Ab27.

For the internalization analysis of SNU449Tp cells with Ab27 and Ab27-hz9, Ab27 (0.3 μg/mL) and Ab27-hz9 (0.2 μg/mL) were used to maintain a similar extent of initial antibody binding to TM4SF5. As a result of the analysis by flow cytometry, it was found that the residual level of cell surface-bound Ab27-hz9 as well as Ab27 was significantly reduced after binding to TM4SF5 (FIG. 26), thus indicating that Ab27-hz9 induced the reduction of the TM4SF5 level on cell surface in a similar manner to Ab27.

From the foregoing, it can be seen that the humanized antibody Ab27-hz9 is fully reactive to TM4SF5 protein and recognizes its target on cell surface more efficiently than the original antibody Ab27.

Example 2-8. In Vivo Antitumor Activity of Ab27-Hz9 in Liver Cancer Xenograft Mouse Model The antitumor efficacy of Ab27-hz9 was evaluated in the SNU449T$_7$ xenograft model. SNU449T$_7$ cells ($3\times10^6$) were subcutaneously injected into the flanks of mice. Ab27-hz9, Ab27, cetuximab, or normal human IgG (300 μg/mouse/dose) was intraperitoneally injected 3 or 4 times per week (12 times in total) into nude mice bearing SNU449T$_7$ xenograft. Ab27-hz9 and Ab27 significantly inhibited tumor growth by about 66% and 62%, respectively, without affecting body weight (FIG. 27), which is comparable to the 59% inhibition induced by cetuximab.

Immunostaining of tumor sections (B of FIG. 27) revealed that the level of proliferative Ki67$^+$ cells was significantly lower in tumors than in tumor growth from control mice, thus indicating that Ab27-hz9 decreased tumor growth by suppressing tumor cell proliferation in a range similar to Ab27.

Example 2-9. In Vivo Tumor Targeting of Ab27 and Ab27-Hz9 in Xenograft Models

In order to validate the tumor-targeting ability of anti-TM4SF5 antibodies, the distributions of Ab27 and Ab27-hz9 after injection into SNU449Tp xenograft model were determined. SNU449T$_7$ cells were subcutaneously injected into the flanks of the nude mice so as to prepare mice bearing tumors. Ab27, Ab27-hz9, and control human IgG were labeled with a fluorescent dye (DyLight 755) and intraperitoneally injected into nude mice bearing SNU449Tp cell-derived tumors. After 96 hours, the distribution of the dye-labeled antibody was quantified by measuring the total photon flux of the fluorescence. As a result, it was found that Ab27 and Ab27-hz9 predominantly localized to the tumors, whereas the control IgG was mostly localized in the liver (FIG. 28).

Additionally, in vivo tumor targeting of Ab27 and Ab27-hz9 were examined using a SNU-398 xenograft mouse model. To confirm in vivo tumor targeting of Ab27 and Ab27-hz9 in endogenous TM4SF5-expressing liver cancer xenografts, SNU-398 cells were subcutaneously injected into the flanks of the nude mice so as to prepare mice bearing tumors. Ab27, Ab27-hz9, and control human IgG were labeled with DyLight 755 were injected into the tail veil of tumor-bearing mice, and fluorescence was measured after 96 hours. Similar to the results of FIG. 28, both antibodies were substantially localized in endogenous TM4SF5-expressing tumors, whereas the IgG was mostly detected in the liver (FIG. 29).

These results suggest that Ab27 and Ab27-hz9 can target TM4SF5-expressing tumor cells in vivo.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

[Sequence Listing]

|  | SEQ ID NO | Kabat numbering | SEQ ID NO | Chothia numbering |
|---|---|---|---|---|
| HCDR1 | 1 | DYEMH | 9 | GYTFTDY |
| HCDR2 | 2 | AIDPETGGTAYNQKFKG | 10 | DPETGG |
| HCDR3 | 3 | PYLGY | | |
| LCDR1 | 4 | RSSQSLVHSNGNTYLH | | |
| LCDR2 | 5 | KVSNRFS | | |
| LCDR3 | 6 | FQGSHIPLT | | |
| VH | 7 | QVQLVQSGAEVKKPGASVK VSCKAS**GYTFT*DYEMH*WV RQAPGQGLEWMG*AIDPET GGTAYNQKFKG*RVTMTADK SISTAYMELSRLRSDDTAVY YCARPYLGYWGQGTLVTVSS | | |
| VL | 8 | EIVLTQSPGTLSLSPGERAT LSCRSSQSLVHSNGNTYLH WYQQKPGQAPRLLIYKVSN RFSGIPDRFSGSGSGTDFTL TISRLEPEDFAVYYCFQGSH IPLTFGQGTKVEIK | | |

SEQUENCE LISTING

```
Sequence total quantity: 10
SEQ ID NO: 1              moltype = AA   length = 5
FEATURE                   Location/Qualifiers
source                    1..5
                          mol_type = protein
                          note = HCDR1_Kabat numbering
                          organism = synthetic construct
SEQUENCE: 1
DYEMH                                                                    5

SEQ ID NO: 2              moltype = AA   length = 17
FEATURE                   Location/Qualifiers
source                    1..17
                          mol_type = protein
                          note = HCDR2_Kabat numbering
                          organism = synthetic construct
SEQUENCE: 2
AIDPETGGTA YNQKFKG                                                       17

SEQ ID NO: 3              moltype = AA   length = 5
FEATURE                   Location/Qualifiers
source                    1..5
                          mol_type = protein
                          note = HCDR3
                          organism = synthetic construct
SEQUENCE: 3
PYLGY                                                                    5

SEQ ID NO: 4              moltype = AA   length = 16
FEATURE                   Location/Qualifiers
source                    1..16
                          mol_type = protein
                          note = LCDR1
                          organism = synthetic construct
SEQUENCE: 4
RSSQSLVHSN GNTYLH                                                        16

SEQ ID NO: 5              moltype = AA   length = 7
FEATURE                   Location/Qualifiers
source                    1..7
                          mol_type = protein
                          note = LCDR2
                          organism = synthetic construct
SEQUENCE: 5
KVSNRFS                                                                  7

SEQ ID NO: 6              moltype = AA   length = 9
FEATURE                   Location/Qualifiers
source                    1..9
                          mol_type = protein
                          note = LCDR3
                          organism = synthetic construct
SEQUENCE: 6
FQGSHIPLT                                                                9

SEQ ID NO: 7              moltype = AA   length = 114
FEATURE                   Location/Qualifiers
source                    1..114
                          mol_type = protein
                          note = VH
                          organism = synthetic construct
SEQUENCE: 7
QVQLVQSGAE VKKPGASVKV SCKASGYTFT DYEMHWVRQA PGQGLEWMGA IDPETGGTAY         60
NQKFKGRVTM TADKSISTAY MELSRLRSDD TAVYYCARPY LGYWGQGTLV TVSS               114

SEQ ID NO: 8              moltype = AA   length = 112
FEATURE                   Location/Qualifiers
source                    1..112
                          mol_type = protein
                          note = VL
                          organism = synthetic construct
SEQUENCE: 8
EIVLTQSPGT LSLSPGERAT LSCRSSQSLV HSNGNTYLHW YQQKPGQAPR LLIYKVSNRF         60
SGIPDRFSGS GSGTDFTLTI SRLEPEDFAV YYCFQGSHIP LTFGQGTKVE IK                 112

SEQ ID NO: 9              moltype = AA   length = 7
FEATURE                   Location/Qualifiers
source                    1..7
```

```
SEQUENCE: 9                mol_type = protein
GYTFTDY                    note = HCDR1_Chothia numbering      7
                           organism = synthetic construct SEQ ID NO: 10              moltype = AA  length = 6
FEATURE                    Location/Qualifiers
source                     1..6
                           mol_type = protein
                           note = HCDR2_Chothia numbering
                           organism = synthetic construct
SEQUENCE: 10
DPETGG                                                         6
```

The invention claimed is:

1. An antibody or antigen-binding fragment thereof, that binds to transmembrane 4 L6 family member 5 (TM4SF5), comprising:
  a heavy chain variable domain comprising the sequence of SEQ ID NO: 7, which comprises HCDR1 comprising the sequence of SEQ ID NO: 9; HCDR2 comprising the sequence of SEQ ID NO: 10; and HCDR3 comprising the sequence of SEQ ID NO: 3; and
  a light chain variable domain comprising the sequence of SEQ ID NO: 8, which comprises LCDR1 comprising the sequence of SEQ ID NO: 4; LCDR2 comprising the sequence of SEQ ID NO: 5; and LCDR3 comprising the sequence of SEQ ID NO: 6,
  wherein the CDR sequences of SEQ ID NOS: 9 and 10 are assigned according to the numbering system of Chothia.

2. The antibody or antigen-binding fragment thereof according to claim 1, wherein the antibody is an IgG antibody.

3. A pharmaceutical composition for preventing or treating TM4SF5-related diseases comprising the antibody or antigen-binding fragment thereof of claim 1.

4. The pharmaceutical composition according to claim 3, wherein the TM4SF5-related diseases are selected from the group consisting of fatty liver, steatohepatitis, liver fibrosis, liver cirrhosis, portal hypertension, liver cancer, stomach cancer, colorectal cancer, rectal cancer, oral cancer, pharynx cancer, larynx cancer, lung cancer, colon cancer, breast cancer, cervical cancer, endometrial cancer, ovarian cancer, prostate cancer, testicular cancer, bladder cancer, kidney cancer, pancreatic cancer, bone cancer, connective tissue cancer, skin cancer, brain cancer, thyroid cancer, leukemia, Hodgkin's disease, soft tissue sarcoma, lymphoma, multiple myeloma, and blood cancer.

5. The pharmaceutical composition according to claim 4, wherein the TM4SF5-related diseases are selected from the group consisting of fatty liver, steatohepatitis, liver fibrosis, liver cirrhosis, portal hypertension, liver cancer, stomach cancer, colorectal cancer, colon cancer, prostate cancer, pancreatic cancer, and soft tissue sarcoma.

6. The pharmaceutical composition according to claim 3, wherein the pharmaceutical composition is administered alone or in combination with any one material selected from the group consisting of 5-fluorouracil (5-FU), oxaliplatin, doxorubicin, sorafenib, and cetuximab.

7. A polynucleotide encoding the antibody or antigen-binding fragment thereof according to claim 1.

8. An expression vector comprising the polynucleotide according to claim 7.

9. A transformant comprising the polynucleotide according to claim 5 or an expression vector comprising the same.

10. A composition for diagnosing TM4SF5-related diseases comprising the antibody or antigen-binding fragment thereof according to claim 1.

11. A method for detecting transmembrane 4 L6 family member 5(TM4SF5)-related diseases comprising detecting TM4SF5 protein in a biological sample through an antigen-antibody reaction using the antibody or antigen-binding fragment thereof according to claim 1.

12. A method for preventing or treating diagnosing transmembrane 4 L6 family member 5(TM4SF5)-related diseases, which includes administering an antibody or antigen-binding fragment thereof according to claim 1 to a subject.

* * * * *